US011103501B2

(12) United States Patent
Deboeck et al.

(10) Patent No.: US 11,103,501 B2
(45) Date of Patent: Aug. 31, 2021

(54) DRY POWDER FORMULATION OF AZOLE DERIVATIVE FOR INHALATION

(71) Applicants: Arthur Deboeck, Gurabo, PR (US); Francis Vanderbist, Beersel (BE); Philippe Baudier, Uccle (BE); Thami Sebti, Braine-le-Comte (BE); Christophe Duret, Bouillon (BE); Karim Amighi, Woluwé Saint Pierre (BE)

(72) Inventors: Arthur Deboeck, Gurabo, PR (US); Francis Vanderbist, Beersel (BE); Philippe Baudier, Uccle (BE); Thami Sebti, Braine-le-Comte (BE); Christophe Duret, Bouillon (BE); Karim Amighi, Woluwé Saint Pierre (BE)

( * ) Notice: Subject to any disclaimer, the term of this patent is extended or adjusted under 35 U.S.C. 154(b) by 0 days.

(21) Appl. No.: 15/724,211

(22) Filed: Oct. 3, 2017

(65) Prior Publication Data
US 2018/0104239 A1   Apr. 19, 2018

Related U.S. Application Data

(63) Continuation of application No. 15/155,699, filed on May 16, 2016, now abandoned, which is a continuation of application No. 13/261,916, filed as application No. PCT/EP2012/074785 on Dec. 7, 2012, now abandoned.

(30) Foreign Application Priority Data

Dec. 9, 2011 (EP) .................... 11192851

(51) Int. Cl.
| | |
|---|---|
| A61K 31/496 | (2006.01) |
| A61K 47/14 | (2017.01) |
| A61K 47/26 | (2006.01) |
| A61K 47/28 | (2006.01) |
| A61K 9/00 | (2006.01) |
| A61K 9/16 | (2006.01) |

(52) U.S. Cl.
CPC .......... *A61K 31/496* (2013.01); *A61K 9/0075* (2013.01); *A61K 9/1617* (2013.01); *A61K 9/1623* (2013.01); *A61K 9/1682* (2013.01); *A61K 9/1688* (2013.01); *A61K 9/1694* (2013.01); *A61K 47/14* (2013.01); *A61K 47/26* (2013.01); *A61K 47/28* (2013.01); *A61K 2300/00* (2013.01)

(58) Field of Classification Search
CPC .. A61K 9/1694; A61K 9/1617; A61K 31/496; A61K 9/1688; A61K 47/14; A61K 47/26; A61K 47/28
See application file for complete search history.

(56) References Cited

U.S. PATENT DOCUMENTS

| | | | |
|---|---|---|---|
| 5,539,021 A | 7/1996 | Pate et al. | |
| 5,688,842 A | 11/1997 | Pate, III et al. | |
| 6,264,922 B1 | 7/2001 | Wood et al. | |
| 6,862,890 B2 | 3/2005 | Williams, III et al. | |
| 7,521,068 B2 | 4/2009 | Bosch et al. | |
| 2002/0037324 A1* | 3/2002 | Vladyka, Jr. | A61K 9/145 424/499 |
| 2003/0049323 A1 | 3/2003 | Hitt | |
| 2004/0105821 A1 | 3/2004 | Bernstein | |
| 2004/0137070 A1 | 7/2004 | Scherzer | |
| 2004/0176391 A1 | 9/2004 | Weers et al. | |
| 2007/0287675 A1 | 12/2007 | Hitt et al. | |
| 2010/0255094 A1 | 10/2010 | Jackson et al. | |

* cited by examiner

*Primary Examiner* — Mina Haghighatian
(74) *Attorney, Agent, or Firm* — William Beaumont; Juneau & Mitchell

(57) ABSTRACT

A spray dried-powder composition for inhalation comprising particles (X) containing (a) between 5 and 50% by weight of at least one azole derivative in amorphous state but not in crystalline structure and (b) at least one matricial agent to the composition selected from a group consisting of polyol such as sorbitol, mannitol and xylitol; a monosaccharides such as glucose and arabinose; disaccharide such as lactose, maltose, saccharose and dextrose; cholesterol, and any mixture thereof, wherein the composition provides a dissolution rate of said azole derivative of at least, 5% within 10 minutes, 10% within 20 minutes and 40% within 60 minutes when tested in the dissolution apparatus type 2 of the United States Pharmacopoeia at 50 rotation per minute, 37° C. in 900 milliliters of an aqueous dissolution medium adjusted at pH 1.2 and containing 0.3% of sodium laurylsulfate.

15 Claims, 7 Drawing Sheets

DRY POWDER FORMULATION OF AZOLE DERIVATIVE FOR INHALATION

FIELD OF THE INVENTION

Aspergillosis refers to the spectrum of pathologies caused by *Aspergillus* species which are filamentous fungi more precisely ascomycetes classified in the form subdivision of the Deuteromycotina.

Invasive aspergillosis (IA) is an advance state of *aspergillus* colonization after conidia germination and is a frequent cause of infectious disease related to morbidity and mortality in immunocompromised (IC) patients. In the past two decades, the incidence rate of IA infections has dramatically increased. For example, from the 80s to 1997, the trend in mortality associated with invasive aspergillosis showed an increase of 357%. Being an opportunistic disease this can be explained by the rising number of IC patients nowadays encountered in clinical practice.

The principal gateway to this pathogen (80 to 90% of IA) and are often the starting points of the invasion that can lead to disseminated state, fatal in more than 90% of cases. The fungus can disseminate after invasion of the pulmonary tissue through the blood stream to reach liver, spleen, kidney, brain and other organs. The invasive state is mainly reach in IC population who after conidia's inhalation has not enough immune defenses (principally macrophages) to prevent their germination and therefore hyphae proliferation (principally neutrophils) through tissues and blood capillaries in the contamination area.

Clinical guidelines recommend the use of amphotericin B as primary treatment of pulmonary invasive aspergillosis. However amphotericin B is not well tolerated, shows a lot of severe adverse reactions. Moreover, inhaled amphotericin B was shown to be ineffective as prophylaxis in patients with prolonged neutropenia following chemotherapy or autologous bone marrow transplantation. For those reasons their use is often contraindicated and the first line therapy, considered as gold standard class, are the azole derivates (itraconazole, voriconazole, posaconazole, ravuconazole). Despite those current therapies (oral and intravenous), once the invasive stage is reached, the mortality rate goes from 50 to 90% (in regards with population's category and study. For most IC patients progression can be terrifically fast (e.g. 7-14 days from onset to death). This high rate of failure can be explained by the conjuncture of several factors. First of all, invasive pulmonary aspergillosis difficult to diagnose in the first stage of the disease and once first manifestations occur advance invasive state is often already reach. Another important reason of failure is that existing therapies (oral, intravenous) induce a lot of side effects and metabolic interactions due to their high systemic exposure necessary to reach suitable pulmonary concentration. Moreover, due to the poor water solubility of azole derivates (e.g. <1 µg/ml for itraconazole), oral therapies show high inter and intra-individual variation in term of bioavailability that can lead to infra therapeutic concentrations in the lung tissue. Another important factor is also to take into account in the explanation of high rate treatment failure. Indeed, for an optimal antifungal activity, minimum inhibitory concentration (MIC) in pulmonary lung epithelium and lung tissue has to be maintained. With conventional therapies (oral, IV) those concentrations may not be reach inside the fungal lesion despite high systemic concentrations.

For those reasons pulmonary delivery can be an interesting alternative for prophylaxis and/or treatment of invasive pulmonary aspergillosis. By delivering antifungals directly to the lung in the infection's site, concentration above the MIC90% could be effectively and directly maintained in the lung tissue while minimizing systemic exposure therefore side effects and metabolic interactions. However, to reach that result the poorly water soluble active ingredient has to be delivered efficiently into the lung and must be dissolved in-situ as much as possible.

Over the years, pulmonary drug delivery has extensively been developed. Interest in this particular route of administration can be justified by the numerous problems it overcomes and the advantages it offers in particular situations. Indeed, pulmonary drug delivery can be effective both for systemic delivery and localized delivery to treat systemic or lung diseases. This non invasive route of administration avoids hepatic first-pass effect which, for example, can lead to active pharmaceutical ingredient (API) inactivation or formation of toxic metabolites. It has been demonstrated that pulmonary drug delivery required smaller doses than by oral route to achieve equivalent pulmonary therapeutic effects. This can be particularly interesting in the case of pulmonary infectious diseases treated by inhalation of anti-infectious drugs (as azole derivates) presenting systemic sides effects and metabolic interactions. Indeed, pulmonary drug delivery allows minimizing systemic concentration, thus side effects, while maintaining effective lung concentration directly to the site of infection. The administration of the anti-infectious drug directly to the lung allows minimization of systemic concentrations therefore drug systemic side effects and metabolic interactions which are very pronounced with common antifungal drugs. Those interactions and side effects are often the reason of treatment failures in the different patient populations.

There are several approaches to achieve oral inhalation (pulmonary delivery). Inhaler devices can be classified in three different types, including liquid nebulizers, pressurized aerosol metered dose inhalers (pMDIs), and dry powder dispersions devices. The two formers are losing interest due to their disadvantages that can be overcome through the use of dry powder inhalers (DPIs). The majors problems encountered in liquid nebulization are the drug instability during storage, the relatively long time to achieve total nebulization, risk of bacterial contamination, high cost, low efficiency and poor reproducibility. Regarding pMDIs one of the principal source of administration's procedure failure is the necessity of synchronization between dose activation and breathing. For those reasons DPIs are nowadays at the top of the research interest in the pulmonary delivery field.

Regarding problems underlying above, the problem to be solved is to provide patients with antifungal inhaled compositions that offer a high lung deposition and allow an adequate dissolution profile of the poorly water soluble active ingredient in-situ, therefore allowing an optimized efficacy of the drug product. Additionally, the inhaled compositions should present an acceptable safety profile, should be stable, should be easy to administer in a reproducible and precise way. The manufacturing process of said composition should be short, simple, cheap, ecological, reliable, and environmentally friendly (no USP class 1 or 2 solvents)

Firstly, an important characteristic that the formulation must possess is an improved and optimal in vitro dissolution profile (compared to the unformulated drug). The manufacturing process must present the flexibility of controlling the dissolution rate of the active ingredient to obtain an optimal pharmacokinetic profile thus providing an optimal therapeutic response. An optimal pharmacokinetic profile corresponds to a maximization of lung time residence while minimizing systemic absorption and elimination. Azole compounds are poorly water-soluble substances (e.g. solubility of itraconazole pH 7<1 µg/ml) and inhalation of an insoluble powder can lead to (i) poor tolerance and/or (ii) lack of efficacy. The low wetability of poorly water soluble active ingredients can cause irritation and inflammation to the pulmonary mucosa after inhalation. Wetability of the inhaled particles must be enhanced. Furthermore, to be effective, antifungal drugs have to reach after administration (in this case by inhalation) a pulmonary concentration that is above the MIC of the concerned fungus. It is commonly recognized that the active form of a drug is the dissolved state. In other words, the dissolved proportion of the inhaled dose has to be maintained in the lung epithelium and lung tissue above the MIC of *Aspergillus*. Then the dissolution rate of the drug will directly influence the proportion of the deposited dose that can play its antifungal activity. As mentioned above, azole compound are poorly soluble and micronized bulk material present an extremely poor dissolution rate. Improvement of its dissolution rate and wetability are here necessary to avoid excessive elimination of the undissolved fraction of the drug by alveolar macrophages in the lower airways and mucociliary clearance in the upper airways. However, acceleration of the dissolution rate of the active ingredient has preferably to be limited to a certain extend because a too fast dissolution rate would result in an excessive absorption of the dissolved fraction to the systemic compartment and thus possibly to adverse event. A need that the invention must satisfy is the possibility to modify the dry powder composition to improve and/or modulate its dissolution rate while keeping good powder flowability and high dispersibility properties. The dissolution rate of the active ingredient must be kept in a determined ranged and it should be possible to make vary the dissolution profile (greater or less amount of dissolved active substance at the same time point within the dissolution range) in order to make vary the in-situ dissolution rate therefore the therapeutic and side effects.

Secondly, antifungal azole compound after oral inhalation has to reach the site of infection. The dry powder should present an optimized aerodynamic behavior. That means than the dry powder must reach the potential conidia's deposition site where fungus can grow and invade peripheral tissue area. Regarding this, it is obvious that after dose actuation from a dry powder inhaler, a determinate fraction of the generated particles have to present an aerodynamic diameter range similar than those of fungal conidia (between 1.9 and 6 µm) to provide to the lung an appropriated antifungal dose. The generated particles from an inhaler device in breath condition must present a high percentage of particles having an aerodynamic diameter less than 6 µm. This percentage will directly influence the dose really reaching the lungs. The aerodynamic behavior of particles is determined by their size and composition. As described above, the formulation must present an optimized dissolution profile to obtain an optimal pharmacokinetic profile in vivo. Once an optimized composition has been developed, it should be possible to modify its aerodynamic behavior in order to modulate powder fine particle fraction to reach a suitable dose deposition that would play correctly its fungal activity (depending on its dissolution rate profile).

Thirdly, another primordial point is to take in consideration. Indeed, after inhalation the dry powder must present a good safety profile and must be compatible with the lung membrane to avoid hyper-responsiveness, cough, airway spasticity or inflammation. Dissolution rate improvement, necessary in this particular case, often needs the use of specific excipients that can cause adverse reaction or that are not suitable for pulmonary administration. Since documentation on the safety profile of inhaled excipient is quiet limited, to avoid pulmonary toxicity after inhalation, the use physiologic component, generally recognized as safe (GRAS) and authorized excipients must be privileged in pulmonary formulations (for example the U.S. Food and Drug Administration (FDA database). This is a real limitation because authorized excipients are quiet limited and mainly endogenous or derivates of endogenous substances to the lung are recognized as GRAS excipient. Moreover considering again the safety profile of the formulation, the manufacturing process should preferentially avoid the use of the United States Pharmacopeial Convention (USP) and European Pharmacopoeia class 1 and 2 solvent due to their high toxicity and low tolerated residual level in pharmaceutical formulations. From an ecological perspective, the used of only class 3 solvent and save excipients considerably reduced pollution and operators hazardous contaminations risks which are no negligible gains. This also reduces the manufacturing cost by reducing the resources that must be implemented to avoid possible contamination of the operators or leaks to the environment.

Fourthly, powder for use in dry powder inhaler must display good flowability, low agglomeration tendency for an easy processing at industrial scale.

Finally, the manufacturing process must be simple, continuous and designed to be realized in one or two step to obtain the final dry product.

There is here a need to develop a simple, flexible process using only GRAS authorized excipient and low toxic potential solvents to produce a dry powder for inhalation to treat pulmonary invasive aspergillosis (i) that allows improvement and/or control of active ingredient's dissolution rate (ii) that allows modification of the aerodynamic behavior of the particle while keeping dissolution rate improvement and/or modification (iii) presenting good flow properties (iv) involving a simple, reliable, reproducible and relatively cheap manufacturing process.

This invention allows producing a dry powder with a high percentage of particles presenting the same aerodynamic diameter that inhaled conidia. This fraction of particles presents an improved and/or controlled dissolution profile compared to unformulated drug. This release profile can be modified by only using endogenous or GRAS substances and low toxicity potential solvents. The whole process is a one or two step procedures.

BACKGROUND OF THE INVENTION

Several approaches to develop a formulation suitable for pulmonary administration of poorly soluble compound have been developed. Majority of those inventions disclose a strategy of process or formulation but none of those satisfied all the needs described above.

Regarding problems underlying above, the problem to be solved is to provide patients with antifungal inhaled compositions that offer a high lung deposition and at the same time allow an adequate dissolution profile of the poorly water soluble active ingredient in-situ, therefore allowing an optimized efficacy of the drug product. Additionally, the inhaled compositions should present an acceptable safety profile, should be stable, should be easy to administer in a reproducible and precise way. The manufacturing process of said composition should be short, simple, cheap, ecological, reliable, and environmentally friendly (no USP class 1 or 2 solvents)

Numerous inventors developed suspensions, nanosuspensions and solutions of poorly soluble active ingredients suitable for nebulization (U.S. Pat. No. 6,264,922 B1, German Pat, Pub. No. 101 45 361 A1, PCT International Pub. No. WO 03035031, PCT international Pub. No. WO 2009/137611 A2). But as previously mentioned pulmonary administration by nebulization presents problems and disadvantages such as drug instability, long time to achieve total dose administration, risk of bacterial contamination, high cost, low efficiency and poor reproducibility. Moreover these strategies, due to inherent solubility of drug nanoparticles, do not allow optimization of drug's dissolution rate.

PCT International Pub. No. WO 2009/106333 A1 describes a new nanosuspension of antifungal azole derivates with improved purity profile. This high purity profile is guaranty by a high quality production process minimizing contamination of the formulation which could come from equipments. This assured minimum toxicity that can be caused by inorganic insoluble impurity.

Canadian Pub. No. 2014401 A1 relates to pharmaceutical compositions for treating invasive fungal infections by inhalation. It describes dry powder for inhalation wherein the micronized active ingredient is blended with an acceptable carrier. Those compositions allow deep penetration of the active ingredient to the lung but do not promote dissolution rate.

Many other research groups have developed interest in the development of a drug formulated as a dry powder for inhalation presenting solubility improvement.

U.S. Pat. No. 6,645,528 B1 discloses a method of fabrication of porous drug matrices presenting a faster dissolution rate than bulk material and no porous drug matrices of the same drug. This matricial product could be administrated by inhalation as a dry powder. In the manufacturing procedure, the active ingredient is dissolved in a volatile solvent to form drug solution. A pore forming agent is combined to the drug solution to form an emulsion, suspension or second solution. The volatile solvent and pore forming agent are then removed (preferably by spray drying) to yield the porous matrix of drug. The pore forming agent can be a volatile liquid or a volatile solid preferably a volatile salt that are immiscible with the volatile solvent. The authors describe that the use of a pore forming agent was the critical characteristic for dissolution rate enhancement of the active ingredient. However they did not mention or demonstrate that by this process in vitro dissolution rate and aerodynamic behavior of inhaled particles could be optimized. Moreover no example of in vitro impaction and dissolution tests specifically designed for dry powder for inhalation were disclosed. In another aspect, solvent and excipient used in all examples were not in concordance with toxicity requirements in the field of pulmonary administration. This concept of formulation has preferentially been developed to produce parenteral formulation that needs a re-dispersion step in solution before administration. U.S. Pat. Appl. Pub. No. 2004/0105821 A1 applied this concept to dry powder for inhalation to produced sustained release formulation for inhalation and included in the description an application to antifungal agents such azole derivates but no examples are provided.

U.S. Pat. No. 7,521,068 B2 describes formulations and associated manufacturing procedure for nanoparticulate dispersion aerosol, dry powder nanoparticulate aerosol formulation, and propellant based aerosol formulations preparation. The aqueous dispersion or dry powder describe therein contained insoluble drug particles (including azole derivates) having a surface modifier on their surface. In the surfaced modifier are included, oraganic and inorganic pharmaceutical excipients. Such excipients include various polymers, low molecular weight oligomers, natural products and surfactant. The dry powder formulation is obtained by drying an aqueous nanosuspension. Prior drying, the aqueous dispersion of drug and surface modifier can contain a dissolved diluent such as sugars.

Regarding our particular situation (maximization of lung residence time while minimizing systemic absorption and elimination) where dissolution rate is primordial, this invention presents sonic disadvantages. Indeed, it was correctly emphasized on the advantage that size reduction has on dissolution rate improvement since there is proportionality between the solid API dissolution rate and its surface area available for dissolution as described by the Nernst-Brunner/Noyes-Whitney equation. But it is not possible with this manufacturing process to modify dissolution rate of the solid nanoparticle present in the formulation. The dissolution rate of the solid API after inhalation would be inherent to nanoparticles dissolution rate which can lead to excessive absorption in the systemic compartment therefore enhancing the probability adverse reactions, drug-drug and metabolic interactions which could induce treatment failure. Nanoparticles dissolution velocity is generally tremendous fast and this invention do not clearly establish the possibility to delay, decrease or control dissolution rate of the active ingredient. Additionally, a surface modifier is necessary for nanosuspension stabilization and it will result in surface wetting enhancement of particles and consequently to their dissolution rate. Moreover, diluents and excipient that can be added prior the drying step of the aqueous nanosuspension are limited to hydrophilic components and cannot be hydrophobic due to the aqueous nature of the described dispersants. Once this diluent will be after inhalation in contact with the aqueous pulmonary surfactant its dissolution will be fast and it would not be possible to modify nanoparticles dissolution rate therefore their systemic absorption leading to an excessive elimination.

PCT International Pub. No. WO 2004/060903 A2 discloses effective lung concentration and residence time specifically for amphotericin B after inhalation to treat or to give a prophylaxis against fungal infection. However, recent data indicates that toxicity related to this formulation type which is a serious limitation for pulmonary administration that cannot be accepted (Spickard and Hirschmann, *Archives of Internal Medicine* 1994, 154(6), 686). Additionally, amphotericin B was shown to be ineffective as prophylaxis in patients with prolonged neutropenia following chemotherapy or autologus bone marrow transplantation. Formulations described therein are lipid complex based formulations of amphotericin B that can be disadvantageous for the azole derivates because of their poor solubility. In the description of the invention azole derivates are included but no examples of this pharmaceutical class were provided. No specific manufacturing procedure was underlined to allow optimization of those concentration and residence time. Lipid/phospholipid based formulations production methods are described but those process are specific to amphotericin B (complex formation) and could not be applied to different compounds such as azole derivates.

U.S. Pat. Appl. Pub. No. 2007/0287675 A1 describes inhalable compositions and methods for making such compositions. Compositions are constituted of one or more respirable aggregates comprising one or more poorly water soluble active agent. After inhalation those composition allow to reach a maximum lung concentration of at least 0.25 μg/g that can be kept for a certain period. The inventors describe a series of methods that can be use to prepare those respirable aggregates. Those methods comprise Ultra rapid freezing (U.S. Pat. Appl. Pub. No. 2004/0137070), Spray freezing into liquid (U.S. Pat. No. 6,862,890), Evaporative precipitation into aqueous solution (U.S. Pat. No. 6,862,890), control precipitation (U.S. Pat. Appl. Pub. No. 2003/0049323), High Internal Phase solutions (U.S. Pat. Nos. 5,539,021 and 5,688,842). They demonstrate in a comparative example the possibility to provide aggregates with different in vitro dissolution rate but not with the same manufacturing process. Their process involves the use of surfactant in determined proportion. Those proportions are fixed in order to generate a controlled particle size and no to modulate the dissolution properties of the drug substance. Neither examples of impaction tests nor in vitro results specifically designed for dry powder for inhalation were disclosed. In all examples provided therein the use of class 1 and 2 solvent, toxic after inhalation, was required for total solubilization of the itraconazole.

Solubilisation of drugs in co-solvents or micellar-solutions is other possibilities to improved and/or modify dissolution rate of poorly soluble active ingredients. However those kinds of formulations are also designed to be administrated by nebulization and not as a dry powder for inhalation. Complexation with cyclodextrin is another strategy to improve dissolution rate of poorly soluble substance when formulated as dry powder for inhalation. However, cyclodextrin have shown after inhalation to induce inflammatory reaction signs and its safety profile is, nowadays, not clear enough. Polymeric surfactants such as co-polymers of polyoxyethylene and polyoxypropylene have been used in several DPI formulations presenting an improved in vitro dissolution rate (McConville et al., 2006). Those polymers have been noted to produce slight alveolitis after 2 weeks of exposure in inhalation toxicity study Formation of salt forms with enhanced dissolution profiles and formation of solid dispersion are also common techniques in formulation field to improve dissolution rate of poorly soluble substances.

Another possibility to improve dissolution rate of a drug is the modification of the physical form of the dry active ingredient. Both nanonizing dry crystalline particles and formation of amorphous dry form of the drug induce an improvement of substance's dissolution rate. However, drying particles generally induce their aggregation and then a loss of dissolution rate improvement due to the decrease in the total surface area available to the dissolution medium. Moreover there is here a need to form particles with a determinate aerodynamic diameter to reach after inhalation the site of infection of the *Aspergillus* colonization site (regarding their aerodynamic diameter). Dispersing those nanosize crystalline and/or amorphous particles in acceptable excipient for inhalation is an interesting approach to form particles with appropriated aerodynamic diameter and to keep dissolution rate improvement of generated dry particles once deposited on the pulmonary mucosa. The nature of the matricial agent should have the properties to enhance or delayed dissolution rate of the active ingredient (compared to another formulation). All excipients and solvent in use have to be physiologically tolerated or recognized as save to minimize potential toxicity after inhalation or during production and reduce hazardous environmental contaminations.

The present invention provides a one or two step procedure to produce this type of dry powder using only safe and authorized excipient/solvent. This dry powder presents good flowability. The produced dry powders present appropriated aerodynamic features (regarding inhaled conidia) once emitted from a dry powder inhaler device. The concept of formulation allows improvement and/or modification/control . . . of the poorly soluble active ingredient dissolution rate to obtain a formulation that will minimize systemic absorption while maximizing its residence time in the lung and hence its efficacy.

SUMMARY OF THE INVENTION

The subject matter of the present invention is defined in the appended independent claims. Preferred embodiments are defined in the dependent claims.

In a first embodiment, the subject matter of the present invention is spray-dried particles (X) for a inhalation composition comprising (a) between 5 and 50% by weight of at least one azole derivative in amorphous state and (b) at least one matricial agent to the composition selected from a group consisting of polyol such as sorbitol, mannitol and xylitol; a monosaccharides such as glucose and arabinose; disaccharide such as lactose, maltose, saccharose and dextrose; cholesterol, and any mixture thereof. Preferably, said matricial agent is mannitol or cholesterol. Advantageously, the weight ratio of azole derivative(s)/matricial agent(s) is between 0.5/99.5 and 40/60, preferably between 1/99 and 35/65, more preferably between 10/90 and 35/65. Said azole derivative do not comprise a compound of the group consisting of omeprazole, esomeprazole, lansaprazole, pantoprazole and rabeprazole.

In particular, said particles further comprise a surfactant and preferably comprise between 0.1 and 5% by weight of the surfactant. Advantageously, said surfactant is selected from lecithin, phospholipids derivatives such as phosphatic acids, phosphatidyl choline (saturated and unsaturated), phosphatidyl ethanol amine, phosphatidyl glycerol, phosphatidyl serine, phosphatidyl inositol, dioleoylphosphatidylcholine, dimyristoyl phosphatidylcholine, dipalmitoylphosphatidylcholine, distearoyl phosphatidylcholine, diarachidoyl phosphatidylcholine, dibenoyl phosphatidylcholine, ditricosanoyl phosphatidylcholine, dilignoceroyl-phatidylcholine, dimiristoylphosphatidylethanol-amine, dipalmitoyl-phosphatidylethanoalamine, pipalmitoleoyl-phasphatidylethanol-amine, distearoyl-phosphatidylethanolamine, dimyristoylphosphatidylglycerol, dipalmitoylphosphatidyl glycerol, dipalmitolcoylphosphatidylglycerol and more preferentially hydrogenated derivates or modified vitamins comprise α-tochopherols derivates.

The subject matter of the present invention is also a spray dried-powder composition for inhalation comprising the particles (X), wherein said composition comprises at least 50% of the matricial agent and provides a dissolution rate of said azole derivative of at least, 5% within 10 minutes, 10% within 20 minutes and 40% within 60 minutes when tested in the dissolution apparatus type 2 of the United States Pharmacopoeia at 50 rotation per minute, 37° C. in 900 milliliters of an aqueous dissolution medium adjusted at pH 1.2 and containing 0.3% of sodium laurylsulfate. Said composition preferably provides a Fine Particle Fraction of the azole derivative of at least 35% of the total nominal dose of the azole in the powder following the method "preparations for inhalation: assessment of fines particles" using the Multi-stage Liquid Impinger, Apparatus C-chapter 2.9.18 of the European Pharmacopoeia.

Advantageously, said composition further comprises another type of particles (Y) which contain (a) between 5 and 50% by weight of at least one azole derivative in amorphous state (b) at least one matricial agent, and (c) a surfactant Said particles (Y) preferably contain between 0.5 and 5% by weight of the surfactant(s).

Advantageously, said composition further comprises another type of particles (Z) which further contain up to 20% by weight of nanoparticles of the azole derivative in crystalline structure having a mean size between 0.1 and 1 µm.

In particular, said composition provides a dissolution rate of the azole derivative of 5 to 50% within 5 minutes, 10 to 60% within 10 minutes, 15 to 90% within 20 minutes and 40 to 100% after 60 minutes.

Preferably, the azole derivative(s) is selected from miconazole, fluconazole, itraconazole, posaconazole, voriconazole, isoconazole, ketoconazole, oxiconazole, bifonazole, fenticonazole, tioconazole, terconazole, sulconazole, ravuconazole, econazole, terconazole, preferably, itraconazole.

The subject matter of the present invention is also a method for preparing said spray dried particles and composition which comprises the following steps of:
a) preparing a liquid composition comprising:
  i. a liquid carrier selected from a class 3 solvent according to European Pharmacopoeia such as acetic acid, heptane, acetone, isobutyl acetate, anisole, isopropyl acetate, 1-Butanol, methyl acetate, 2-Butanol, 3-Methyl-1-butanol, Butyl acetate, methylethylketone, tert-Butylmethyl ether, methylisobutylketone, cumene, 2-Methyl-1-propanol, dimethyl sulfoxide, pentane, ethanol, 1-Pentanol, Ethyl acetate, 1-Propanol, ethyl ether, 2-Propanol, ethyl formate, propyl acetate, formic acid, or the mixture thereof, or the mixture of such solvent with water ;
  ii. at least one azole derivative in solution in said liquid carrier; and
  iii. at least one matricial agent in solution in said liquid carrier,
wherein the weight ratio of azole derivative(s)/matricial agent(s) is between 0.5/99.5 and 40/60, preferably between 1/99 and 35/65, more preferably between 10/90 and 35/65,
b) spray drying the liquid composition for producing particles for the dry powder composition.

Preferably, said method further comprises the steps of:
c) preparing another liquid composition comprising a liquid carrier selected from a class 3 solvent or any mixture of two or more solvents with or without water and at least one matricial agent in solution in said liquid carrier, wherein the liquid composition further comprises:
  i. at least one azole derivative in solution in said liquid carrier and at least one surfactant; and/or
  ii. nanoparticles of at least one azole derivative having a mean size between 0.1 and and 1 µm,
d) spray drying said liquid composition provided by step (c) for producing particles for the dry powder composition; and
e) physically blending the particles obtained by steps (b) and (d).

The subject matter of the present invention is also a liquid composition comprising:
  i. a liquid carrier selected from a class 3 solvent according to European Pharmacopoeia such as acetic acid, heptane, acetone, isobutyl acetate, anisole, isopropyl acetate, 1-Butanol, methyl acetate, 2-Butanol, 3-Methyl-1-butanol, Butyl acetate, methylethylketone, tert-Butylmethyl ether, methylisobutylketone, cumene, 2-Methyl-1-propanol, dimethyl sulfoxide, pentane, ethanol, 1-Pentanol, Ethyl acetate, 1-Propanol, ethyl ether, 2-Propanol, ethyl formate, propyl acetate, formic acid, or the mixture thereof, or the mixture of such solvent with water;
  ii. at least one azole derivative in solution in said liquid carrier; and
  iii. at least one matricial agent in solution in said liquid carrier,
wherein the weight ratio of azole derivative(s)/matricial agent(s) is between 0.5/99.5 and 40/60, preferably between 1/99 and 35/65, more preferably between 10/90 and 35/65.

Preferably, said liquid composition further comprises at least one surfactant and/or nanoparticles of at least one azole derivative having a mean size between 0.1 and 1 µm.

Figure 11:
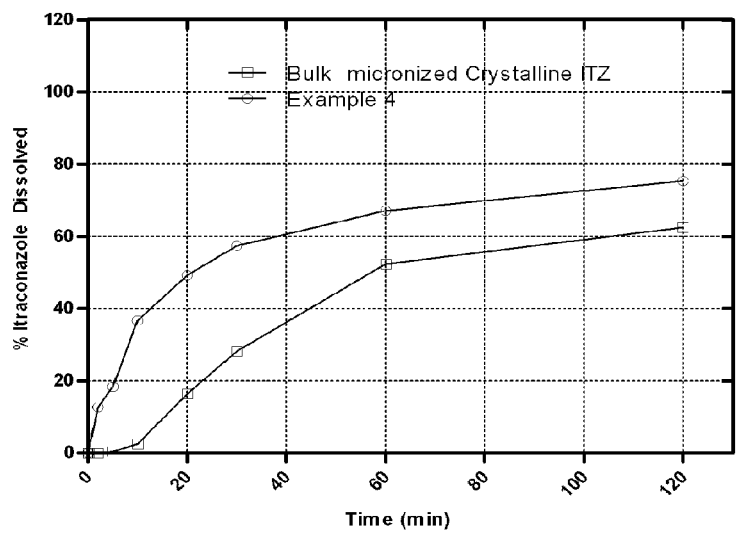

FIG. 11 is in vitro dissolution profile of micronized crystalline bulk itraconazole and a spray dried powder formulation according to the present invention comprising Itraconazole, cholesterol and phospholipon (example 4).

Figure 12:
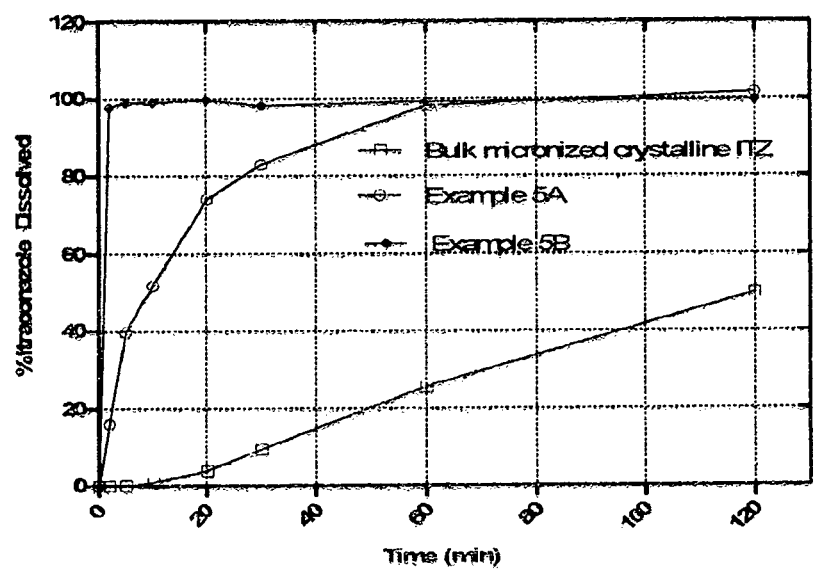

FIG. 12 is in vitro dissolution profile of micronized crystalline bulk itraconazole and spray dried powder formulations comprising itraconazole and mannitol according to the present invention, i.e., particles not containing crystalline nanoparticles of itraconazole (example 5A) and particles containing crystalline nanoparticles of itraconazole (example 5B).

DESCRIPTION OF THE INVENTION

This invention is related to a dry powder formulation for inhalation of azole derivatives with the proviso that said azole derivative is not a compound of the group consisting of the family of omeprazole, esomeprazole, lansaprazole, pantoprazole and rabeprazole and a process to provide it.

Azole derivatives can be selected from the group consisting of miconazole, fluconazole, itraconazole, posaconazole, voriconazole, isoconazole, ketoconazole, oxiconazole, bifonazole, fenticonazole, tioconazole, terconazole, sulconazole, ravuconazole, econazole, terconazole.

The dry powder of the invention can present high dispersibility capabilities to maximize, after inhalation from an inhaler device, the proportion of particles presenting an appropriated aerodynamic diameter range.

Appropriated aerodynamic range refers to aerodynamic diameter that presents inhaled conidia. Generated particles from an inhaler device in breath conditions must present the same aerodynamic range that inhaled *aspergillus* conidia (1.9-6 μm) to reach potential infections sites for an optimal treatment targeting and effectiveness.

Advantageously, the dry powder composition is based on the use of exclusively physiological component excipients, safe, generally recognized as save (GRAS) excipients, FDA authorized excipients for inhalation therapy to guaranty a good safety profile after inhalation and to be compatible with the lung membrane to avoid hyper-responsiveness, cough, airway spasticity or inflammation.

The manufacturing process requires one or two step(s) to obtain the final dry product and all techniques used are made for an easy scaling up to industrial batch size production. The dry powder in itself is designed to possess enhanced flow properties for an easy processing at industrial scale.

The dry powder is specifically designed for oral inhalation to treat or give prophylaxis against pulmonary invasive aspergillosis. The azole derivatives are in form that allows that dissolution rate can be improved at different extent and/or modified by varying the composition of the dry powder. The improvement can be controlled by modifying the dry powder composition and/or the active pharmaceutical ingredient (API) physical state or by combining prior administration different embodiments of the invention.

This is advantageous because the modification of dissolution rate can overcome in Vivo clearance and absorption mechanisms that lead to decreasing drug proportion in the site of infection.

The dry powder is constituted of matricial microparticles. The matricial microparticles are constituted of safe, physiological component or inhalation FDA authorized excipient wherein the active ingredient is dispersed in a modified physical state. After inhalation of those microparticles, after matrix dissolution or erosion, the active ingredient will expose a higher surface area to the pulmonary mucosa than the same dose of pure spray dried active ingredient microparticles, resulting in an improved dissolution rate.

The nature of the matricial agent directly influences the dissolution profile of the active ingredient. The matricial agent can be (i) hydrophilic to directly release the active ingredient when in contact with the pulmonary mucosa (ii) hydrophobic to delay the release of the active ingredient (iii) a mixture of hydrophilic and hydrophobic (in different proportion) agent to obtain an intermediate release profile.

Matricial agents are physiological component excipients, GRAS excipients; FDA authorized excipients for inhalation therapy to avoid as far as possible pulmonary or systemic toxicity. The matricial agents can be combined together to confer to the dry powder desired flow, aerodynamic and dissolution characteristics. The matricial agent is necessary in the composition.

Matricial agent can be selected from the group consisting of sugar alcohols, polyols such as sorbitol, mannitol and xylitol, and crystalline sugars, including monosaccharides (glucose, arabinose) and disaccharides (lactose, maltose, saccharose, dextrose) and cholesterol.

In one embodiment of the invention the API is in majority in amorphous state. The proportion of amorphous active ingredient (in percentage of the total amount of active ingredient from the invention is from 51% to 100%, preferably between 70% and 100%, even more preferably 100%.

One way to obtain an amorphous compound is to spray dry it from a solution because the rapid solvent evaporation during the drying process do not let enough time to solid particles to recrystallize. However azole compounds and particularly itraconazole are only sparingly soluble in chloride solvent such as dichloromethane and chloroform which are, due to their high toxicity, not recommended for the preparation of pharmaceutical formulations. This invention provides methods to obtain an amorphous product by spray drying the API from a solution using only a class 3 solvent. Those solvents are considered as low toxic potential solvents and then offer a better safety profile in case of residuals inhalation. This category of solvent includes acetic acid, Heptane, Acetone, Isobutyl acetate, Anisole, Isopropyl acetate,1-Butanol, Methyl acetate, 2-Butanol, 3-Methyl-1-butanol, Butyl acetate, Methylethylketone, tert-Butylmethyl ether, Methylisobutylketone, Cumene, 2-Methyl-1-propanol, Dimethyl sulfoxide, Pentane, Ethanol, 1-Pentanol, Ethyl acetate, 1-Propanol, Ethyl ether, 2-Propanol, Ethyl formate, Propyl acetate, formic acid or the mixture thereof, By spray drying an organic solution of active ingredient it is possible to obtain it after the drying process in an amorphous state with geometric size appropriated for inhalation therapy (<5 μm). This can be done from a drug saturated organic solution. However solubility of azole derivates such as itraconazole in class 3 solvents is extremely low. These low concentrations could not be optimal for a good recovery of the dry powder after spray drying In order to obtain a good recovery of the dry powder after spray drying azole derivatives with a higher solubility may be selected instead of itraconazole. A matricial agent can be added before spray drying this kind of solutions to enhance total solute concentration. An acid can be added into—a preheated organic class 3 solvent under magnetic stirring in order to enhance the solubility of poorly soluble azole compound such as itraconazole. An organic solution comprising azole compound(s) can also be heated to high temperature under magnetic stirring to obtain enhanced solubility of the azole compound(s). Those options only allow the dissolution of hydrophobic excipients in the solution . . . A determinate quantity of water can be added to one of those solutions type in order to allow dissolving both poorly soluble active ingredients, hydrophilic and hydrophobic excipients. This can be particularly interesting in order to modify active ingredient's dissolution rate, particle size, aerodynamic behavior and flow properties. Preferential ratio of water to organic solvent (in volume to volume percentage) are from 0 to 50%, preferably between 0% to 30%, more preferably between 10% and 30% and even more preferably between 20% and 30%.

On a thermodynamic point of view, due to their unorganized structure, amorphous compounds present the advantage to possess higher solubility than the same crystalline compound. In practice, during dissolution, amorphous compounds often recrystallize to lower energy crystalline state presenting lower solubility than the initial product. This invention provides formulations wherein an active compound is in an amorphous state and formulated so that its dissolution occurs before complete drug recrystallization leading to an improved dissolution rate product. Indeed, the improvements and enlargement of surface area of dry powder formulation arrived at local site of a patient can be obtained by spray drying a solution of an active ingredient together with a hydrophilic matricial agent which provides particles comprising the active ingredient in amorphous state dispersing in the matricial agent. Such improvements in surface area can—accelerate the active ingredient dissolution rate preventing from excessive recrystallization prior dissolution.

Recrystallization of amorphous drugs also may happen during storage leading to a decrease of the dissolution performance product. One aspect of the present invention provide a stable amorphous product when formulate as a solid dispersion of the active ingredient in a matricial agent.

In a composition of the invention, the amount of azole derivates that can be incorporated in the matricial agent(s) is from 0.5 to 40%, preferably from 1 to 35%, more preferably from 10 to 35% by weight.

Surprisingly, it is possible by varying the concentration of the spray dried solution or the matricial agent/API ratio to modify aerodynamic behavior of generated particles. Varying the concentration in solution or the matricial agent/API ratio can directly modify the geometric diameter and the density of dried particles thus their aerodynamic diameter which will also directly modify their aerodynamic behavior. Modifying one of those parameters would lead to formation of particles presenting different aerodynamic behavior while presenting similar dissolution rate. This can help to provide a dry powder with an optimized dissolution rate that will penetrate the lung in a sufficient quantity to provide appropriated antifungal dose from a predetermined nominal dose. Variation of those parameters allows then the optimization of the fine particle dose (FPD) of the spray dried powder while keeping improved dissolution rate.

Preferably, the amount of the azole derivative added in the liquid composition is between 0.1% and 5%, preferably between 0.5% and 2% by weight of the azole derivative to the volume of the liquid composition (g/100 mL).

A surfactant can be added in the matrix of particles comprised in a dry powder formulation according to the present invention in order to improve the dissolution rate enhancement of the active ingredient. A surfactant is an amphiphilic compound with both hydrophilic and hydrophobic characteristics. By spray drying a solution containing both the active ingredient the matricial agent and a surfactant it is possible to produce matricial microparticles wherein the active ingredient and the surfactant are dispersed. The surfactant will play a wetting enhancement effect on the active ingredient resulting, in a reduction in particle agglomeration and acceleration/improvement of its dissolution rate when compared to matricial microparticles without surfactant.

The surfactant(s) can be selected from the group consisting of physiological component, GRAS (generally recognized as save) excipients, FDA authorized excipients for inhalation therapy to avoid any pulmonary or systemic toxicity.

The quantity of added surfactant could influence azole compound dissolution rate improvement. The preferred amount of surfactant is comprised between 0.1 and 5% by weight in the dry powder composition.

Preferentially surfactant can be phospholipids, lecithin, lipids or GRAS modified vitamins, or combination of such surfactant. Phospholipids that may use comprise phosphatic acids, phosphatidyl choline (saturated and unsaturated), phosphatidyl ethanol amine, phosphatidyl glycerol, phosphatidyl serine, phosphatidyl inositol. Examples of such phospholipids include, dioleoylphosphatidylcholine, dimyristoyl phosphatidylcholine (DMPC), dipalmitoylphosphatidylcholine (DPPC), distearoyl phosphatidylcholine (DSPC), diarachidoyl phoshatidylcholine (DAPC), dibenoyl phosphatidylcholine (DBPC), ditricosanoyl phosphatidylcholine (DTPC), dilignoceroylphatidylcholine (DLPC), dimiristoylphosphatidylethanolamine (DMPE), dipalmitoylphosphatidylethanoalamine (DPPE), pipalmitoleoylphasphatidylethanol amine, distearoylphosphatidylethanolamine (DSPE), dimyristoylphosphatidylglycerol (DMPG), dipalmitoylphosphatidyl glycerol (DPPG), dipalmitolcoylphosphatidylglycerol and more preferentially hydrogenated derivates. Examples of GRAS modified vitamins comprise α-tochopherols derivates.

A too high quantity of surfactant in the formulation can induce an important particle size increase during spray drying. Due to their low melting point, surfactants could soft or melt during spray drying increasing particle size. Dilution of the surfactant in the matricial agent can mask this effect resulting in production of smaller particles with appropriate characteristics.

One particular embodiment of the invention consists to obtain the active ingredient in the form of crystalline nanoparticles by a method described in the art.

The term "nanoparticles" used to describe the present invention has a meaning of solid discrete particles ranging in size from 1 nm to 1000 nm. The presence of the crystalline nanoparticles of azole derivative in a spray dried particle and the weight ratio of the crystalline nanoparticles comprised in the particle can be determined by using powder X-ray diffraction, and differential scanning calorimetry concomitantly with HPLC drug quantification.

Those nanoparticles are then dispersed in a matricial agent to confer to the formulation appropriated particle size, flow properties, dissolution rate and aerodynamic behavior. The dissolution rate of those nanoparticles is instantaneous (within 5 minutes) with a very pronounced burst effect that cannot be delayed due to inherent dissolution rate of the nanoparticles.

The production of this formulation types (i.e., particles containing crystalline nanoparticles of the active ingredient and the matricial agent) includes two steps in the manufacturing procedure. The first step being the production of drug nanoparticles and the second step being the drying procedure. The nanoparticles could be produced by a method described in the art. Preferably nanoparticles are produced by high pressure homogenization. The matricial agent can be added prior the size reduction step or before the spray drying procedure.

In one particular embodiment of the invention the active ingredient is dispersed in the matricial agent both in form of crystalline nanoparticles and amorphous compound. This embodiment can be the result of the spray drying of both matricial agent and the active ingredient in solution together with nanoparticles of the active in. Another aspect of this embodiment is that the dry powder formulation according to the present invention is manufactured by a simple blend of the nanoparticles of the active ingredient, which are obtained by spray drying of a suspension comprising its crystalline nanoparticles and a matricial agent or by mechanical milling of the crystalline active ingredient, and an amorphous matricial formulation obtained by spray drying of the active ingredient in solution. This blend powder will be filled in capsule, blister or multidose device.

The desired result is to confer to the formulation a controlled dissolution profile by optimizing the proportion of nanoparticles/amorphous compound in the formulation. This dissolution profile could not be reach with only the nanoparticles in the formulations. The modification of the proportion nanoparticles/amorphous allow varying dissolution profile. Preferably, the ratio (w/w) of amorphous matricial particles/nanocrystalline matricial composition is comprised between 100/0 to 80/20.

In another embodiment the active ingredient is dispersed as nanoparticles or microparticles in a matrix of the same active ingredient. The active ingredient matricial being in amorphous state Nanosuspension could be concomitantly spray dried with a solution of active ingredient containing a matrix former. The differences that exist between amorphous and nanoparticles dissolution rate could allow modifying dissolution rate of the formulation. The API in solution could either be used as matrix former encapsulating the nanoparticles. This could provide formulation presenting an interesting dissolution rate and optimal aerodynamic characteristics.

EXAMPLES

Example 1

The starting material is constituted of crystalline micronized itraconazole (ITZ) with a volume mean diameter of 3.5 µm and 90% of particles below 6.2 µm. Pure amorphous itraconazole (Example 1A) and a hydrophilic matricial formulation of itraconazole dry powder (Example 1B; invention) were produced at laboratory scale by spray-drying using a Büchi Mini Spray Dryer B-191a (Büchi laboratory-Techniques, Switzerland). Two feed stock solutions were prepared then separately spray-dried in the following conditions: spraying air flow, 800 l/h; drying air flow, 35 m$^3$/h; solution feed rate, 2.7 g/min; nozzle size, 0.5 mm; Inlet temperature, 90° C.; resulting outlet temperature of 53° C. The composition of the feedstock solutions is summarized in Table 1. Each component were dissolved under magnetic stirring (600 rpm) in a hydro-alcoholic solution (20 water-80 isopropanol) heated at 70° c. During spray drying the solutions were kept at a temperature between 60 and 70° C.

TABLE 1

Composition of spray dried solutions in Example 1.

| liquid composition | Itraconazole (g) | Mannitol (g) | Isopropanol (ml) | Water (ml) |
|---|---|---|---|---|
| Example 1A (Comparative: Cex) | 0.56 | — | 80 | 20 |
| Example 1B (Invention: INV) | 0.56 | 1 | 80 | 20 |

Crystallinity profile of the dried samples was evaluated using MDSC (modulate temperature differential scanning calorimetry) and PXRD (powder x-ray diffraction). Those two techniques are complementary and provide a maximum of information on sample's polymorphism.

MDSC experiments were conducted using a Q 2000 DSC (TA Instruments) equipped with cooling system. MDSC differs from standard DSC in the possibility to apply two simultaneous heating rates to the sample, a sinusoidal modulation is added to the linear heating ramp. The total measured heat flow corresponds to the standard heat flow in classic DSC. MDSC heating conditions offers the possibility to make the deconvolution of reversing and non reversing heat flow in which particular thermal event can be singularly detected. Crystallizations phenomena were then observed in the non-reversing heat flow, glass transitions were observed in the reversing heat flow while melting were observed in total heat flow All samples were analyzed in the same following conditions. A 2-3 mg sample was exactly weighted in a low mass aluminum hermetic pan. A 5° C./min temperature rate with a modulation of +/−0.8° C. every 60 seconds was applied to the sample from 25° C. to 185° C. The instrument was calibrated for temperature using indium as a standard. The heat flow and heat capacity signals were calibrated using a standard sapphire sample. The Universal Analysis 2000 software was used to integrate each thermal event.

PXRD is a powerful tool widely used to evaluate the crystalline form of various compounds. It can help to determine the structural physical state of a product. At a given crystalline lattice, will correspond a given PXRD spectra and inversely a given chaotic system (as amorphous state) would not provide any diffraction peak. This will therefore help to evaluate the polymorphic form obtained after spray drying and in a second time to estimate the proportion of amorphous phase within a sample. The powders were analyzed by the Debye-Scherrer method. The samples were submitted to the Kα line of copper, monochromatic radiation (λ=1.540 Å). The diffractometer (Siemens D5000, Germany) equipped with a mounting said reflection Bragg-Brentano, connected to the monochromator and a channel program Diffracplus. The measures are determined to 40 KV, 40 mA in 2theta an angular range from 2° to 60° in steps of 0.02° through a counting speed of 1.2 s per step and a rotation speed of 'sample of 15 rpm. Each sample was stored in a hermetic plastic container and placed at 8, 25, 40° C. They were analyzed directly after spray drying, and after 2 months storage at the different temperatures.

It is possible to quantify the percentage of crystalline phase in a given compound. Several techniques of calculation have been developed In this case measuring the areas under the curves was used to determine the percentage of amorphous phase in the sample. Indeed, there is a proportional relationship between the ratio of the area under the curve of the diffraction peaks above the deviation from the baseline ($A_c$) and the total area of the diffractogram ($A_{tot}$) with the amount of crystalline phase in the sample. To calculate the degree of crystallinity within a sample it suffices to measure the area under the curve of the diffraction peaks ($A_c$) without integrating the deviation from the baseline because it comes from the noise and amorphous areas present in the sample. Then integrate the total area under the curve of the diffractogram ($A_T$). The percentage of crystalline phase will be expressed as in equation 1. The amorphous content expressed in % was estimated as 100% minus the estimated crystallinity degree.

$$\% \text{ Crystailinity} = \left(\frac{A_C}{A_T}\right) \times 100 \qquad \text{Equation 1}$$

Figure 1:
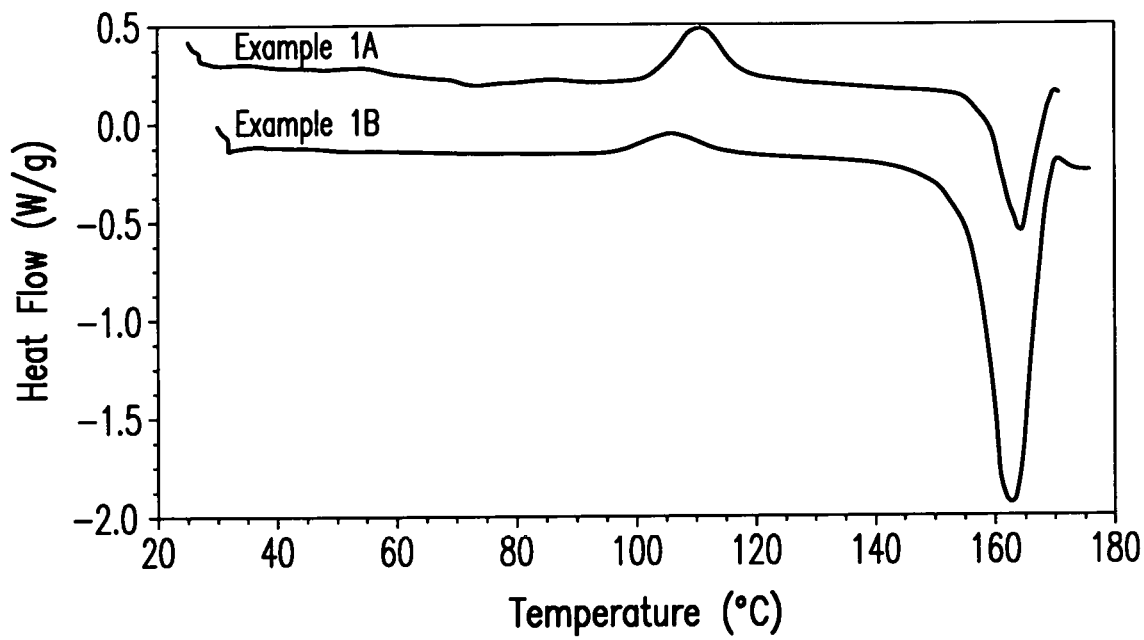
FIG. 1 is the MDSC heating curves of spray dried itraconazole.

MDSC analysis (FIG. 1) showed that amorphous itraconazole (Example 1A) exhibited a glass transition at about 49° C.

An exothermic recrystallization peak was observed between 100° C. and 125° C., which was followed by an endothermic peak around 164° C. that corresponded to the melting of early formed crystalline material. This crystalline itraconazole melted at a temperature lower that the bulk material when analyzed in the same conditions (about 168° C.). Those thermal events are characteristics of glassy itraconazole.

PDRX confirmed amorphous state of itraconazole in Examples 1A and 1B. At T 0 month no diffraction's peak appeared on diffractogram of Example 1A. Approximated calculated amorphous phase in this sample was equal to 100%. This traduced the lack of any crystalline structure in the sample.

TABLE 2

| DRX based estimated amorphous sample's content |  |  |
|---|---|---|
| Formulation | T 0 months | T 2 months |
| 8° C. |  |  |
| Example 1A (Cex) | 100% | 100% |
| Example 1B (INV) | 52% | 52% |
| 25° C. |  |  |
| Example 1A (Cex) | 100% | 100% |
| Example 1B (INV) | 52% | 55% |
| 40° C. |  |  |
| Example 1A (Cex) | 100% | 63% |
| Example 1B (INV) | 52% | 55% |

No recrystallization occurred after 2 months of storage at 8, and 25° C. The percentage of amorphous phase stayed at 100% and no diffraction's peak characteristics of crystalline itraconazole were observed in the diffractograms. When stored at 40° C. amorphous itraconazole recrystallized and approximated amorphous phase shifted to 63%. Recrystallization peaks appeared at the originals diffraction's angles of bulk crystalline itraconazole signifying that amorphous itraconazole recrystallized to its original more stable form.

At T 0, Example 1B's diffractogram exhibited some diffractions peaks. However none of those peaks corresponded to crystalline itraconazole. Diffraction profiles of both α, β and δ mannitol were present. Total approximated amount of amorphous phase within the sample was equal to 52%. This value was higher than actual content of itraconazole in the sample. This came probably from the proportion of mannitol that was amorphous after spray drying. When stored at 8° C., 25° C. and 40° C. only small variations in the approximated amorphous phase in the sample was observed (see Table 2). Contrary to Example 1A, no recrystallization evidences of itraconazole were present at its characteristics diffractions angles. Dispersing amorphous itraconazole in mannitol (by spray drying a solution containing both components) yielded to the stabilization of the amorphous API.

Aerodynamic behavior of generated particles after dose actuation from a dry powder inhaler was assed using a multistage liquid impinger (MsLI). The dry powder inhaler used was an Axahaler® (SMB laboratories). A flow rate (adjusted to a pressure drop of 4 kPa) of 100 L/min during 2.4 sec was applied through the device for each actuation. The device was filled with HPMC n°3 capsules loaded with an approximate quantity of dry powder corresponding to 2.5 mg of itraconazole. One test was realized with three discharges. After the three dose actuations the total deposited dry powder was quantified for each part of the impactor with a suitable and validated HPLC method. Each test was replicated three times. For each test the fine particle dose (FPD) has been estimated by the method described in the European Pharmacopeia 7.2 for aerodynamic assessment of fine particle, apparatus C (MsLI). The expressed results have been weighted to a constant itraconazole nominal dose of 2.5 mg. The fine particle fraction (FPF) is the FPD expressed in % of the nominal dose.

A Malvern Spraytec® laser diffraction equipment was used to measure particle size distribution (PSD) during the aerodynamic fine particle assessment test. The laser beam was directly placed between the throat and the impactor to measure the PSD of generated dry powder cloud, which was then split along its aerodynamic diameter in the MsLI during simulated inhalation conditions. The average PSD was measured from three replicates of each sample. Results were expressed in terms of D[4.3], d(0.5) and d(0.9) which are, respectively, the volume mean diameter and the size in microns at which 50% and 90% of the particles are smaller than the rest of the distribution. Results are expressed in Table 3.

TABLE 3

Size and aerodynamic characteristics of the different formulations: Particle Size Characteristics (Mean ± SD, n = 3) Measured with the the Spraytec ® and fine particles fractions (% of particle with $d_{ac}$ < 5 μm) expressed in function of nominal dose (FPF; Mean ± SD, n = 3) measured by impaction test (MsLI).

| | Spraytec ® | | | MsLI |
|---|---|---|---|---|
| Formulation | d(0.5) (μm) | D[4.3] (μm) | d(0.9) (μm) | FPF (%) |
| Example 1B (INV) | 2.22 ± 0.11 | 2.75 ± 0.39 | 3.38 ± 0.28 | 46.9 ± 1.9 |

Particle size analysis revealed that the volume mean diameter of the invention was below 5 μm which is the first criteria for deep lung deposition. This was confirmed by the aerodynamic fine particle assessment test. The invention presented a high FPF equal to 46.9±1.9%.

Dissolution tests were performed using USP 33 type 2 paddle apparatus (Distek Dissolution System 2100C, Distek Inc., USA). The dissolution media was constituted of desionized water set at pH 1.2 (HCl 0.063N) containing 0.3% of sodium lauryl sulfate. This dissolution allowed maintaining SINK conditions throughout the test. The medium was heated to 37° C. and kept at this temperature during the test. The paddle speed was set at 50 rpm and the dissolution vessel was filled with 900 ml of dissolution media. An exactly weighted amount of dry powder corresponding to 10 mg of itraconazole was spread on the dissolution media (=T0). Itraconazole was quantified at pre-determined intervals (0, 2, 5, 10, 20, 30, 60, and 120 minutes) using a suitable validated HPLC method. Five milliliters of dissolution media was removed from the dissolution vessel and directly replaced by fresh dissolution medium. These five milliliters were directly filtered through 0.2 µm diameter filters to avoid quantification of undissolved particles at the determinate time interval. The cumulative amount of drug release was calculated and expressed in percentage of initial drug load and plotted versus time. Each test was replicated three times.

Figure 2:
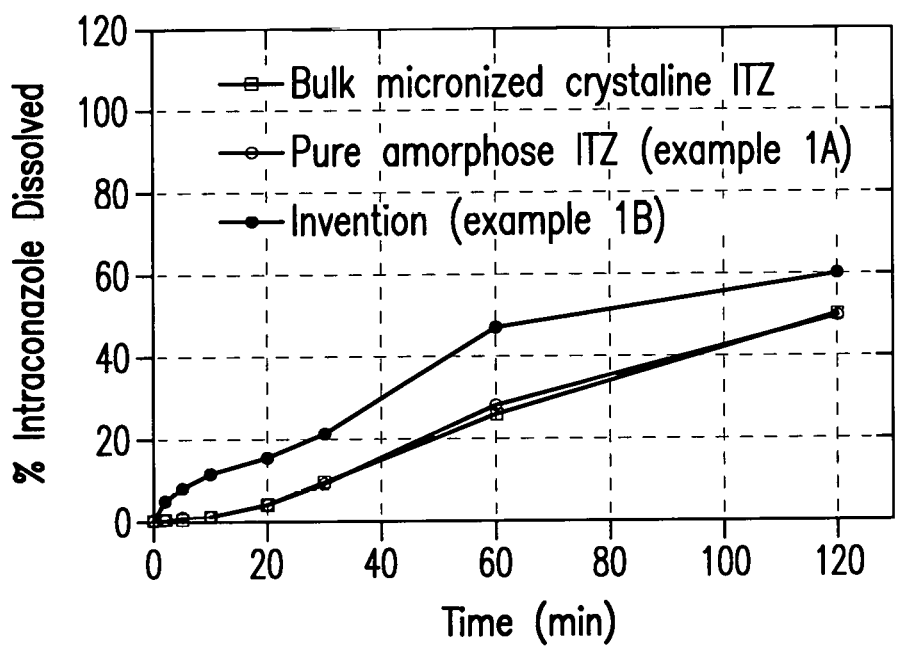
FIG. 2 is in vitro dissolution profile of micronized crystalline bulk itraconazole, pure amorphous itraconazole and a spray dried powder formulation according to the present invention (example 1B) comprising hydrophilic matricial and itraconazole.
Figure 3:
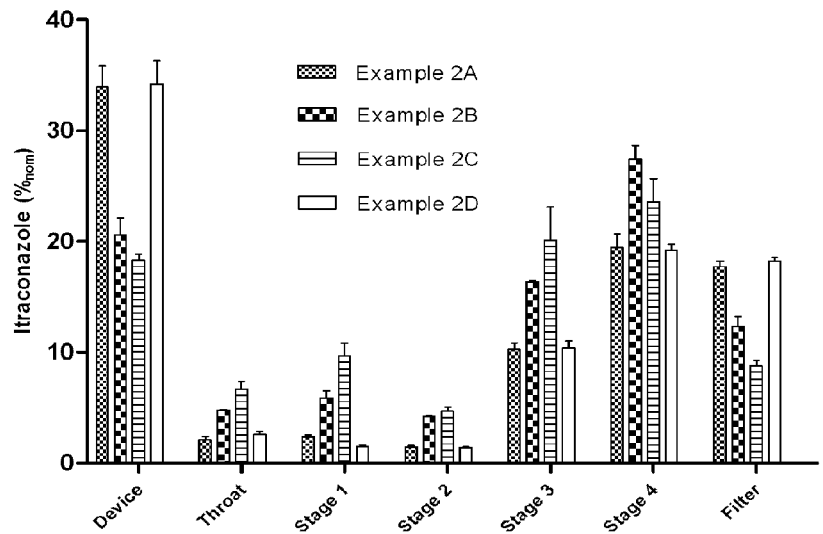
FIG. 3 is in vitro deposition patterns (mean ±S.D, n=3) of spray dried powder formulations according to the present invention (examples 2A to 2D) determined with an MsLI from the Axhaler® device. Results are exposed as percentage of itraconazole (expressed in function of the nominal dose) recovered from the device and each part of the impactor (throat, stage 1, 2, 3, 4 and the filter). The following conditions were used: 100 ml/min, 2.4 s. Three No.3 HPMC capsules filled with a quantity of formulation corresponding to 2.5 mg of itraconazole were used per test.

Dissolution profiles are shown in FIG. 2. Comparison of the dissolution curves of crystalline micronized (bulk ITZ) and pure amorphous ITZ (Example 1A) suggested no difference in the drug release curves. This observation was interesting, since amorphous ITZ would be expected to have a faster dissolution profile compared to the crystalline ITZ. This may come from the fact that the highly hydrophobic nature of the drug substance could lead to poor wetability by the aqueous dissolution media impeding drug dissolution improvement.

Progressive re-crystallization of amorphous ITZ could also have occurred during dissolution, delaying dissolution of the amorphous form. However, it was surprisingly discovered that the formulation of Example 1B according to the present invention wherein ITZ is dispersed in mannitol microparticles provided a significant improvement of the dissolution rate of ITZ, i.e., 11.4% at 10 min, 15.2% at 20 min and 46.7% at 60 min, compared to bulk micronized crystalline ITZ and pure amorphous ITZ. The increase in surface area available to the dissolution media of amorphous ITZ, when dispersed in mannitol microparticles could explain this significant acceleration (FIG. 2) of dissolution rate. Mannitol being dissolved quasi instantly, it was supposed that remaining ITZ particles exposed a higher surface area to the dissolution media that pure spray dried amorphous particles. Mannitol formed spherical matrix wherein amorphous ITZ is dispersed. Once the mannitol is dissolved, porous amorphous ITZ particles are released in the dissolution vessel whit, due to numerous pores formed by the mannitol dissolution. The increased surface area available to the dissolution media increases dissolution rate and prevents excessive re-crystallization which enhance solubility therefore dissolution rate.

Example 2

The purpose of this example was to demonstrate the ability of the invention to modify aerodynamic behavior of the dry powder without modifying its dissolution rate by modifying excipient/API ratio and the total solute in the liquid composition for spray drying.

Four formulations were prepared at laboratory scale by spray-drying using a Büchi Mini Spray Dryer B-191a (Büchi laboratory-Techniques, Switzerland). Four feed stock solutions were separately prepared and spray dried. A determined quantity of itraconazole and mannitol (see Table 4) were dissolved in 100 ml of a hydro-alcoholic solution (20 water-80 isopropanol) heated at 70° C. under magnetic stiffing (600 rpm). The total dry product amount in solution for Examples 2A and 2B are similar (1.56 g). The only difference between the two formulations is the ratio of itraconazole/mannitol. For formulation 2A, 2C and 2D the ratio of itraconazole/mannitol was constant but the total amount of solute in solution in the liquid composition was different. The spray drying conditions are the same that in Example 1.

TABLE 4

Amount of itraconazole and mannitol in the liquid compositions for spray drying in Example 2

| Liquid composition | Composition (for 100 ml) |
|---|---|
| Example 2A (INV) | Itraconazole 0.56 g<br>Mannitol 1 g |
| Example 2B (INV) | Itraconazole 0.234 g<br>Mannitol 1.326 g |
| Example 2C (INV) | Itraconazole 0.28 g<br>Mannitol 0.5 g |
| Example 2D (INV) | Itraconazole 0.84 g<br>Mannitol 1.5 g |

Crystallinity profile of samples was assed using PXRD (powder x-ray diffraction) at the same condition that those described in Example 1.

The diffractograms of the four formulation presented some diffraction's peaks. However none of those diffraction's peaks corresponded to crystalline itraconaozole. That means that itraconazole, in those formulations, was in an amorphous state. Mannitol was in majority in crystalline state. Its three different polymorphic forms (α, β and δ) were present in all samples but in different proportions, the δ form being in majority.

Powder flowability was evaluated by Carr's compressibility index (CI) as described in Example 1. A Carr's index values of above 40% are generally related to poor powder flowability whereas value under 20% are related to extremely good powder flowability. The four present a CI value ranging from 20.9% to 28.8%. Those values indicate good powder flowability for both formulations.

Particle size distribution of powders was evaluated by laser scattering using a Malvern Mastersizer 2000® (Malvern instrument) via a Sirocco 2000® (Malvern instrument) dry feeder dispersion unit. Particle size measurement was done on a sample of +/−50 mg at a pressure of 4 Bar with a feed rate vibration set at 40%. Those conditions allow to measure particle size distribution of practically, totally desagglomerated powder due to very drastic dispersion conditions. Particle refractive index with a real part equaling 1.48 and imaginary part of 0.1 were chosen. Those values ensure low weighted residual (<2%) which traduces result's integrity.

A Malvern Spraytec® was used as describe in example 1. For both techniques, the average PSDs was measured from three replicates of each sample. Results were expressed in terms of D[4.3], d(0.5) and d(0.9) which are, respectively, the volume mean diameter and the size in microns at which 50% and 90% of the particles are smaller than the rest of the distribution. Results are expressed in Table 5.

Aerodynamic behavior of generated particles was evaluated by impaction test as described in Example 1. The fine particle fraction is the FPD expressed in % of the nominal dose (FPF) having an aerodynamic diameter inferior to 5 μm. The emitted doses have been calculated and correspond to the recovered dose from the induction port and five stages of the MsLI during the tests. The emitted dose is express in percentage of the nominal dose and corresponds to the percent of the nominal dose that effectively leaved the device and capsule. Results are expressed in Table 6 and represented in FIG. 3.

Malvern Sirocco® measurements showed that the four formulations exhibited similar mass median diameter d(0.5), and the volume mean diameter values (D[4.3]) of the formulations 2B and 2C were higher than those of the two other formulations as expressed in Table 5. The formation of slightly larger particles seemed occurred in those two formulations. In addition their deagglomeration seemed to be more difficult regarding higher d(0.5) and D[4.3] values obtained for the 2B and 2C formulations with Spraytec® analysis in simulated breath conditions.

Regarding those results it is possible to modify aerodynamic behavior of generated particles by modifying active ingredient/matrix former ratio, the total amount of solute or the concentration of the active ingredient in solution of the spray dried solution while keeping similar dissolution profile. The modification of the aerodynamic behavior was done without varying excipient type or spray drying parameters.

TABLE 5

Size characteristics of the different formulations of Example 2: Particle Size Characteristics (Mean ± SD, n = 3) were Measured with the Malvern Masterzizer2000 ® and Spraytec ®

| | Malvern Sirocco ® | | | Spraytec ® | | |
|---|---|---|---|---|---|---|
| Formulation | d(0.5) (μm) | D[4.3] μm | d(0.9) (μm) | d(0.5) (μm) | D[4.3] (μm) | d(0.9) (μm) |
| Example 2A (INV) | 0.74 ± 0.01 | 1.00 ± 0.04 | 1.78 ± 0.09 | 2.22 ± 0.11 | 2.75 ± 0.39 | 3.38 ± 0.28 |
| Example 2B (INV) | 0.73 ± 0.03 | 1.2 ± 0.46 | 1.89 ± 0.49 | 2.99 ± 0.11 | 6.45 ± 1.78 | 14.91 ± 9.94 |
| Example 2C (INV) | 0.76 ± 0.03 | 1.54 ± 0.18 | 3.08 ± 0.75 | 2.70 ± .05 | 4.60 ± 0.62 | 7.12 ± 2.20 |
| Example 2D (INV) | 0.76 ± 0.01 | 1.01 ± 0.04 | 1.86 ± 0.12 | 2.16 ± 0.04 | 2.31 ± 0.04 | 2.90 ± 0.03 |

Despite their higher particle size and their lower deagglomeration efficiency, the 2B and 2C formulations have higher FPF than formulations 2A and 2D. This is directly related to higher emitted dose for those two formulations (2B and 2C). Because of extremely fine granulometry, despite lower deagglomeration tendency and slightly larger particle size those two formulations penetrated deeper in the impactor than formulation 2A and 2D which result in higher FPF.

TABLE 6

Particle deposition, FPD and FPF (mean ± SD) and emitted dose (% nominal dose) obtained during impaction test (MSLI, 100 l/min, 2.4 sec, 3 discharges per test, nominal dose weighted at 2.5 mg, n = 3).

| | Example 2A | Example 2B | Example 2C | Example 2D |
|---|---|---|---|---|
| Mean FPD (mg) | 1.17 ± 0.05 | 1.40 ± 0.01 | 1.36 ± 0.09 | 1.19 ± 0.04 |
| Mean FPF (%) | 49.6 ± 1.9 | 56 ± 0.4 | 54.4 ± 1.8 | 47.6 ± 1.6 |
| Emitted dose$_{nom}$ (%) | 53.3 ± 1.9 | 71 ± 0.5 | 73.5 ± 6.3 | 53.3 ± 1.5 |

This shows the possibility of this flexible one step process to vary aerodynamic behavior of particles without modify API dissolution rate. All excipients used were GRAS. The four formulations presented good powder flowability.

Example 3

The purpose of this example was to show the ability of the invention to modify dissolution rate's acceleration of a formulation while keeping good flow properties and aerodynamic characteristics.

Three formulations were produced at laboratory scale by spray drying feed stock solutions using a Büchi Mini Spray Dryer B-191a (Büchi laboratory-Techniques, Switzerland). For the five examples a determined quantity of itraconazole, mannitol and hydrogenated soy-lecithin with more than 90% of hydrogenated phosphatidylcholine (Phospholipon 90H), (see Table 7) were dissolved in 100 ml of an hydro-alcoholic solution (20 water:80 isopropanol) heated at 70° c under magnetic stirring (600 rpm). The spray drying conditions are the same that in Example 1.

TABLE 7

Theoretical composition of spray dried solutions, dry formulations ns used during the spray drying process in Example 3.

| | Liquid composition | | | Dry powder composition | | |
|---|---|---|---|---|---|---|
| Formulation | ITZ % (w/v) | Mannitol %(w/v) | PL90H % (m/m$_{ITZ}$) | ITZ (% w/w) | Mannitol (% w/w) | PL90H (% w/w) |
| Example 3A (INV) | 0.56 | 1 | — | 35.9 | 64.1 | — |
| Example 3B (INV) | 0.1 | 0.9 | — | 10 | 90 | — |
| Example 3C (INV) | 0.56 | 1 | 1 | 35.77 | 63.87 | 0.36 |
| Example 3D (INV) | 0.56 | 1 | 10 | 34.65 | 61.88 | 3.47 |
| Example 3E (INV) | 0.1 | 0.9 | 10 | 9.90 | 89.11 | 0.99 |
| Example 3F (Cex) | 0.56 | — | — | 100 | — | — |

Figure 4:
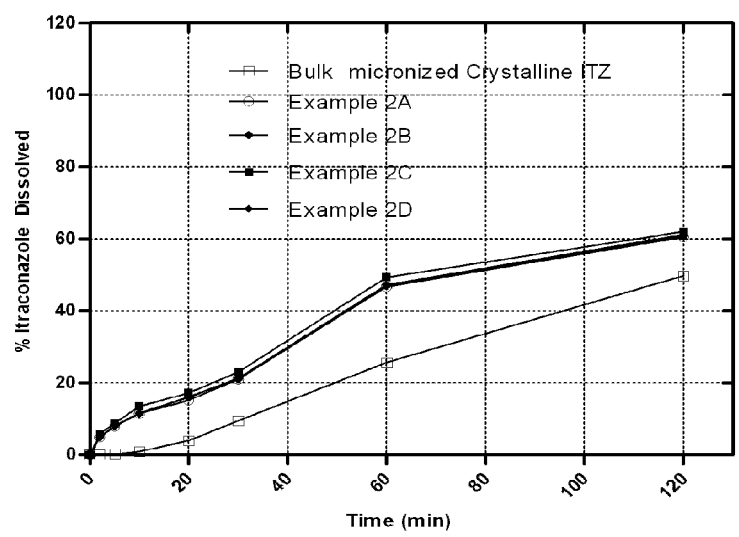
FIG. 4 is in vitro dissolution profile of bulk crystalline itraconazole and the spray dried formulations according to present invention (examples 2A to 2D).
Figure 5:
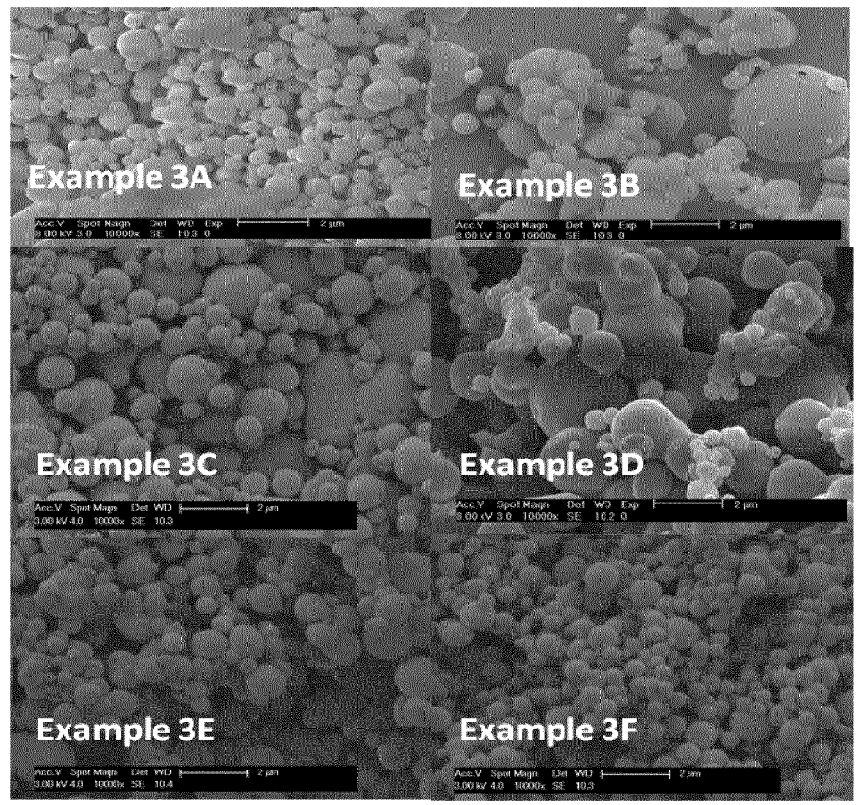
FIG. 5 is the SEM photographs of spray dried powder formulations according to the present invention (examples 3A to 3E) and a spray dried itraconazole (example 3F) at magnification ×1000.
Figure 6:
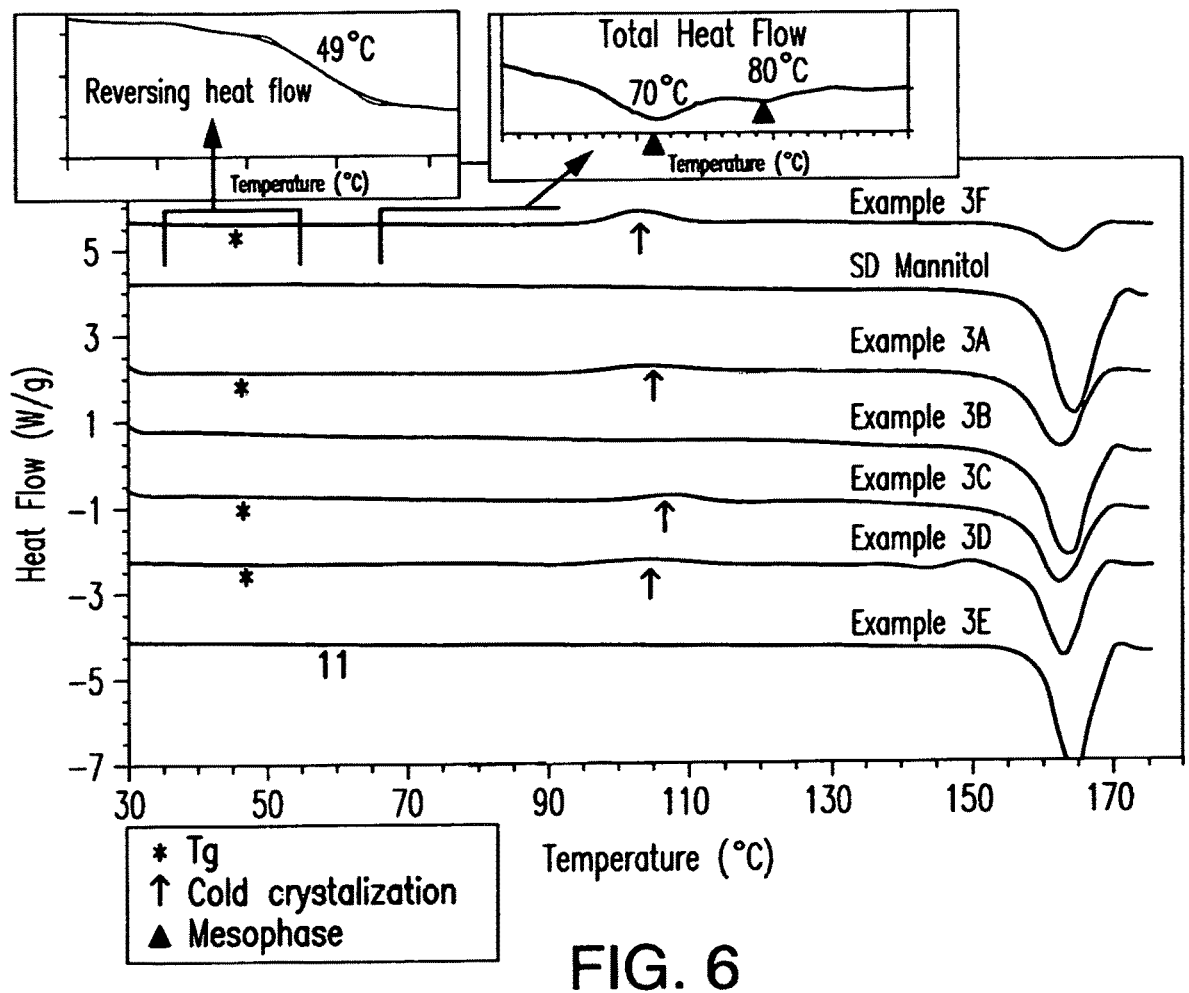
FIG. 6 is the MDSC heating curves of spray dried powder formulations according to the present invention (examples 3A to 3E), spray dried itraconazole (example 3F) and spray dried mannitol.
Figure 7:
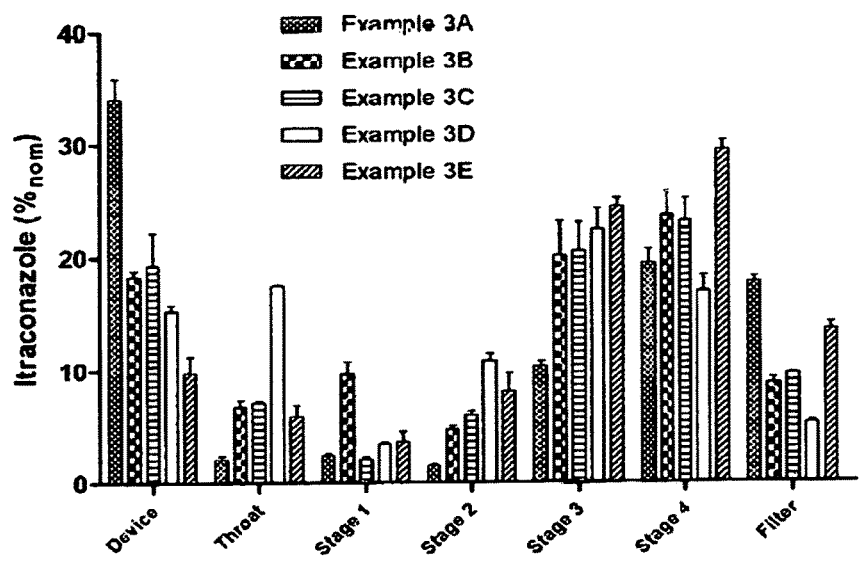
FIG. 7 is in vitro deposition patterns (mean ±S.D, n=3) of spray dried powder formulations according to the present invention (examples 3A to 3E) determined with an MsLI from the Axhaler® device. Results are exposed as percentage of itraconazole (expressed in function of the nominal dose) recovered from the device and each part of the impactor (throat, stage 1, 2, 3, 4 and the filter). The following conditions were used: 100 ml/min, 2.4 s. Three No.3 HPMC capsules filled with a quantity of formulation corresponding to 2.5 mg of itraconazole were used per test.
Figure 8:
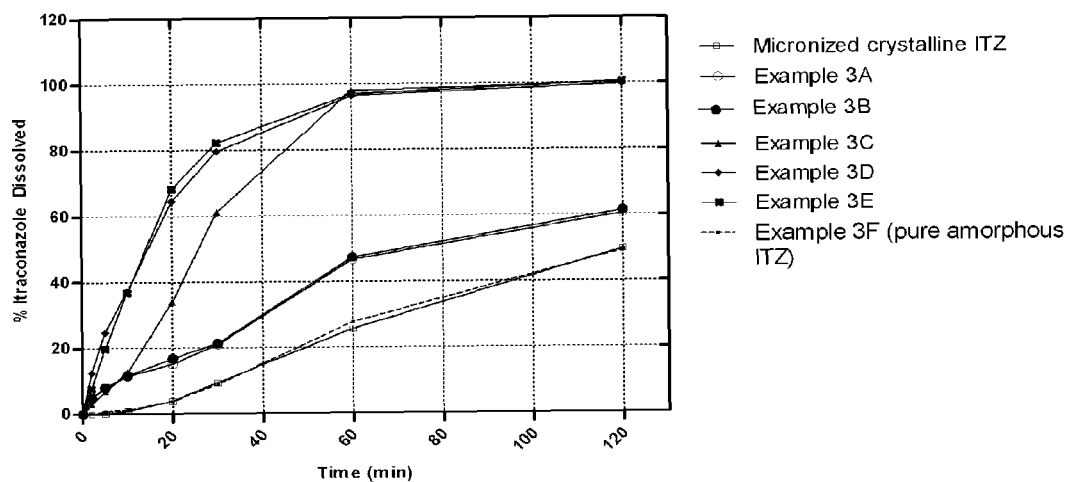
FIG. 8 is in vitro dissolution profile of micronized crystalline bulk itraconazole, spray dried amorphous itraconazole (example 3F) and spray dried powder formulations according to the present invention (examples 3A to 3E).
Figure 9:
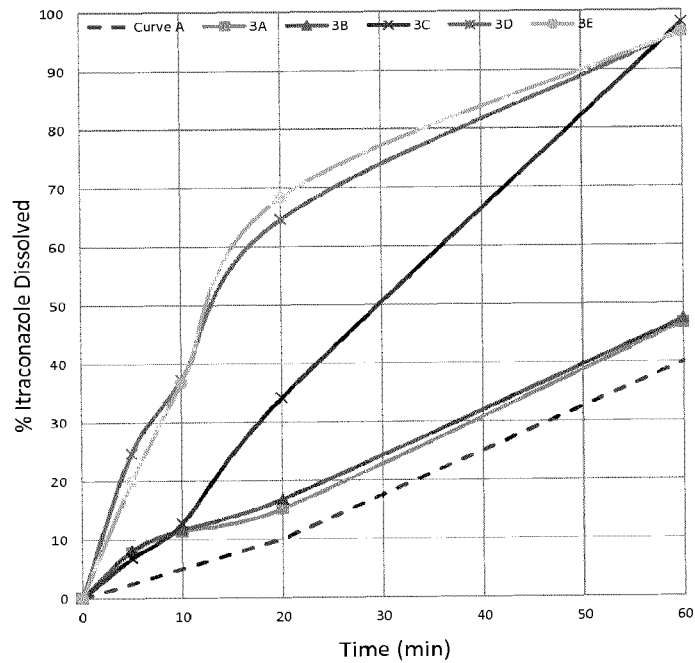
FIG. 9 is in vitro dissolution profile of spray dried powder formulations according to the present invention (examples 3A to 3E) with Curve A defining the dissolution rate of 5% within 10 minutes, 10% within 20 minutes and 40% within 60 minutes.
Figure 10:
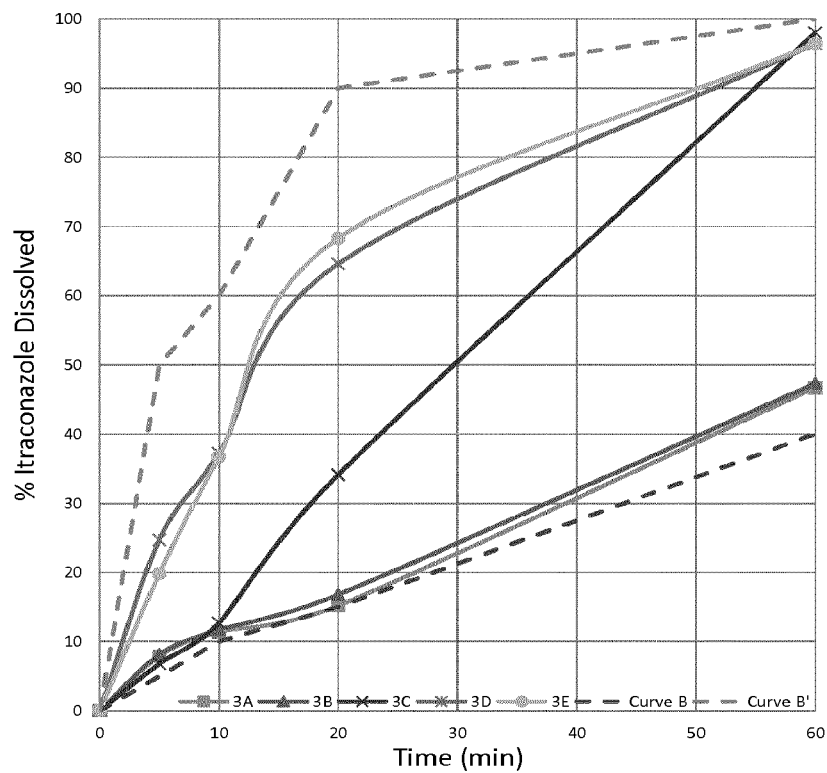
FIG. 10 is in vitro dissolution profile of spray dried powder formulations according to the present invention (examples 3A to 3E) with Curves B and B' defining the dissolution rate of 5% within 5 minutes, 10% within 10 minutes, 15% within 20 minutes and 40% within 60 minutes, and the one of 50% within 5 minutes, 60% within 10 minutes, 90% within 20 minutes and 100% within 60 minutes, respectively.

Dissolution tests were conducted as described in Example 1. Obtained dissolution profiles are shown in FIG. 4. The four formulations exhibited different and faster dissolution's rate than bulk micronized crystalline itraconazole (FIG. 4). The dissolution profiles of Examples 2A, 2B, 2C and 2D were similar.

Determination of drug content was used in order to compare expected and actual drug content. For that a determined quantity of dry powder was dissolved in a dilution phase and sonicated during 20 min Those solutions were analyzed by HPLC-UV from which the drug content (wt %) was determined. Average content (wt %) and standard deviations were calculated from five analysis. Itraconazole content measurements results for the different formulations are summarized in Table 8. The measured values were very close to the expected one with relative errors ranged between −3.9% and 3.0%. Lower itraconazole content as well as introduction of phospholipids in the formulations induced a reduction of this relative error. The active ingredient seemed to be uniformly distributed within particles since samples have been selected randomly and that variation coefficient for all five test samples were not greater than 3.25%. Those exact ITZ contents values were used during aerodynamic particle size analysis to determine exact nominal doses. No ITZ degradation seemed to occur during the spray drying process. The relative error between the measured and expected ITZ content for pure spray dried itraconazole (Example 3F) was equal to 0.7%.

TABLE 8

ITZ content measured by HPLC determination of spray dried powder of Example 3 (mean +/− SD; n = 5)

| Formulation | Measured ITZ content (wt %) | Coefficent variation (%) | Expected ITZ content (wt %) | Relative error (%) |
|---|---|---|---|---|
| Example 3A (INV) | 34.5 ± 0.6 | 1.64 | 35.9 | −3.9 |
| Example 3B (INV) | 9.99 ± 0.3 | 3.25 | 10 | −0.1 |
| Example 3C (INV) | 35.6 ± 0.7 | 1.82 | 35.8 | −0.6 |
| Example 3D (INV) | 33.6 ± 0.7 | 2.01 | 34.65 | −3.1 |
| Example 3E (INV) | 10.2 ± 0.2 | 1.98 | 9.9 | 3.0 |
| Example 3F (Cex) | 100.7 ± 1.6 | 1.61 | 100 | 0.7 |

Qualitative morphological evaluations were conducted by scanning electron microscopy using a Philips XL30 ESEM-FEG (FEI, The Netherlands). The samples were spread on a carbon adhesive band then coated with gold at 40 mA for 90 sec at 6.10-2 mbar under argon. Observations were done at acceleration between 5 and 25KV depending on the sample.

Regarding the quantitative composition of the spray dried formulations, mannitol was the major component and was therefore subject to forming matricial particles within which were dispersed the ITZ and, if applicable, the PL. The morphological evaluation showed that very small spherical particles (~1-2 μm with presence of submicron size particles) with smooth surfaces were formed from the spray dried solution containing mannitol and itraconazole without PL (Examples 3A and 3B; FIG. 5). No morphological differences were observed between these formulations despite the different proportions of amorphous content and mannitol polymorphs. However Example 3B seems to be constituted of slightly larger spherical particles. The presence of PL induces the formation of larger particles with a granular appearance. For the formulation presenting the highest PL content (Example 3D), this granular appearance was the more pronounced and interparticular links were observed (FIG. 5). Those links were probably formed during the spray drying process because of the softening or melting of PL inducing particle aggregation. The reduction of the PL content (Examples 3C and 3E) considerably reduced this grainy aspect.

The residual moisture and solvent content of the different dry powders was assessed using thermogravimetric analysis (TGA) with a Q500 apparatus (TA instruments, New Castle, USA) and Universal Analysis 2000 version 4.4A software (TA Instruments, Zellik, Belgium). The residual water and solvent content was calculated as the weight loss between 25° C. and 125° C. and expressed as a percentage of the initial sample mass. Run were set from 25° C. to 300° C. at a heating rate of 10° C./min on sample mass of about 10 mg and performed in triplicate. Weight loss measured during heating the samples between 25° C. and 125° C. were very low (<0.5%) for each formulations.

MDSC were realized as described in Example 1 and results are show in FIG. 6. As previously described (Example 1A), spray dried in those conditions MTDSC analysis showed that itraconazole was retrieved in its particular amorphous glassy state after the spray drying process (here Example 3F). This particular profile was also observed again on MDSC thermograms for the formulations containing the highest proportion of itraconazole (Examples 3A, 3C and 3D; FIG. 6). The glass transition at about 49° C. was present in the reversing heat flow as was the cold crystallization exotherm at around 100° C. in the non-reversing heat flow. Those thermal events were not detected in the formulations containing the smallest proportion of itraconazole (~10%; Examples 3B and 3E), probably due to lack of sensitivity of the thermal detection for diluted compositions. Spray-dried mannitol and itraconazole melted (total heat flow) at around the same temperature. One single melting point at about 164° C. was observed for all formulations. One supplementary endothermic peak followed by an exothermic peak around 150° C. was observed for Example 3E. These transitions correspond to the melting of δ-mannitol followed by crystallization into the β polymorph. The other formulations did not exhibit this thermal event probably because mannitol was only almost totally (98.5%) in the δ form in this formulation (see PXRD results).

PXRD analyses were conducted on all spray dried powders as described in Example 1. Amorphous contents calculated using the area under the diffractograms are summarized in Table 9. Formulation with higher ITZ content exhibited higher amorphous content. A good correlation was obtained between calculated amorphous content and itraconazole measured content by HPLC ($R^2$>0.9).

the proportion of participation of each mannitol polymorph to the formation of the total crystalline network was evaluated using the reference intensity ratio methodology. Calculations were made on Diffracplus EVA software. This semi-quantitative method of estimation consists of the identification of the different phases in a specimen by comparison with references patterns (from ICDD data base) and the relative estimation of the proportions of the different phases in the multiphase specimens by comparing peak intensities attributed to the identified phases.

TABLE 9

PXRD based estimated amorphous content and α β and Δ mannitol

| Formulation | Amorphous content (%) | α mannitol (%) | β mannitol (%) | Δ mannitol (%) |
|---|---|---|---|---|
| Example 3A (INV) | 55 | 42 | 2.5 | 55.1 |
| Example 3B (INV) | 34.5 | 38.3 | 1.3 | 60.3 |
| Example 3C (INV) | 53 | 31.4 | 2.9 | 65.7 |
| Example 3D (INV) | 57 | 1.1 | 0.4 | 98.5 |
| Example 3E (INV) | 37 | 20.5 | 0.9 | 78.8 |
| Example 3F (Cex) | 100 | — | — | — |

One specific diffraction peak was chosen for each polymorph were no other crystalline structure that could be present in the dry powder diffracted. Specific diffraction peaks at 43.92, 16.81 and 22.09° 2θ were used for α, β and δ-mannitol, respectively and their respective ICDD spectrum were adjusted to those diffractions ray for calculation.

The results are expressed as an estimation of the percentage of each polymorph in the formulations and are summarized in Table 9.

Flow properties were evaluated by determining the Carr's index compressibility index (CI) as described in Example 2. Good powder flowability is a necessary characteristic for an eventually easy processing at an industrial scale. Moreover, more specifically to dry powder for inhalation, a good flowability has already been related to generate an adequate metering, dispersion and fluidization of a dry powder from an inhaler device. All formulations exhibited CI values ranged between 15.6% and 26.4% (see Table 10) which indicated good potential in flow properties for this formulations type.

Particle size analyses were conducted using two different methods. The first method (using a Malvern Mastersizer2000®) provided size results corresponding to totally individualized particles. The second method (using a Malvern Spraytec®) allowed evaluating the size of particles in a deagglomeration rate that is produced after dispersion form an inhaler device.

Malvern Mastersizer2000® results showed that all formulations presented a very fine granulometry with a volume mean diameter ranged from 1.00 μm to 2.04 μm and a mass volume median diameter comprised between 0.74 μm and 1.81 μm (Table 10). The PSD of formulations without PL, Examples 3A and 3B, were very close with a d(0.5) value of 0.74 μm and 0.88 μm, respectively. However, as observed by SEM a small proportion of larger particles were formed for Example 3B, which was traduced by an increase in the D[4.3] and d(0.5).

TABLE 10

Size, aerodynamic and flow characteristics of formulations obtained fromt he different solutions: Particle Size Characteristics (Mean ± SD, n = 3) Measured with the Mastersizer 20000 ® and the Spraytec ®, Emitted dose (expressed in % of nominal dose) and fine particles fractions (% of particle with dae < 5 μm) measured by impaction test (Mean ± SD, n = 3, Carr's index value (CI) (Mean ± SD, n = 3).

| | Laser light scattering | | | | | | |
|---|---|---|---|---|---|---|---|
| | Mastersizer 2000 ® | | Spraytec ® | | Aerodynamic evaluation | | |
| Formulation | d(0.5) (μm) | D[4.3] (μm) | d(0.5) (μm) | D[4.3] (μm) | ED ($\%_{nom}$) | FPF ($\%_{nom}$) | CI (%) |
| Ex. 3A | 0.74 ± 0.01 | 1.00 ± 0.04 | 2.2 ± 0.1 | 2.8 ± 0.4 | 53.3 ± 1.9 | 46.9 ± 1.9 | 26.4 ± 0.1 |
| Ex. 3B | 0.88 ± 0.07 | 1.15 ± 0.05 | 2.71 ± 0.08 | 3.66 ± 0.07 | 81.9 ± 0.6 | 67.0 ± 1.0 | 20.6 ± 0.8 |
| Ex. 3C | 1.35 ± 0.01 | 1.59 ± 0.01 | 2.97 ± 0.04 | 3.14 ± 0.08 | 68.3 ± 7.8 | 52.5 ± 4.9 | 18.1 ± 2.1 |
| Ex. 3D | 1.81 ± 0.05 | 2.04 ± 0.05 | 4.63 ± 0.01 | 5.27 ± 0.07 | 75.2 ± 4.6 | 43.0 ± 5.2 | 24.9 ± 0.9 |
| Ex. 3E | 0.93 ± 0.01 | 1.23 ± 0.04 | 3.14 ± 0.09 | 3.93 ± 0.40 | 84.9 ± 5.3 | 66.4 ± 3.6 | 15.6 ± 1.9 |

Aerodynamic fine particle assessment was done as described in Example 2. Results are shown in Table 10. For all formulation the FPF was calculated to be up to 40% and even up to 60% for the Examples 3B and 3E. In other words, more than 40% of loaded formulations into the device would be deposited in the potential deposition site of inhaled fungal spores after emission from the device. Deposition pattern are exposed in FIG. 7.

Dissolution tests were conducted in the conditions described in Example 1. Every formulations presented different and faster dissolution rate than amorphous spray dried itraconazole (Example 3F) and crystalline bulk ITZ (FIG. 8). As shown in FIG. 9, all dissolution rates of ITZ according to the present invention, 3A to 3E, are at least 5% within 10 minute, 10% within 20 minutes and 40% within 60 minutes when tested in the dissolution apparatus type 2 of the United States Pharmacopoeia at 50 rotation per minute, 37° C. in 9000 milliliters of an aqueous dissolution medium adjusted at pH 1.2 and containing 0.3% of sodium laurylsulfate, namely these dissolution rates are found in the upper area of the curve A which defines the dissolution rate of 5% within 10 minute, 10% within 20 minutes and 40% within 60 minutes. As shown in FIG. 10, the dissolution rates of ITZ according to 3A to 3E are also included in an area between curves B and B', which defines the dissolution rate of 5% within 5 minute, 10% within 10 minute, 15% within 20 minutes and 40% within 60 minutes, and the one of 50% within 5 minute, 60% within 10 minute, 90% within 20 minutes and 100% within 60 minutes, respectively, when tested in the dissolution apparatus type 2 of the United States Pharmacopoeia at 50 rotation per minute, 37° C. in 9000 milliliters of an aqueous dissolution medium adjusted at pH 1.2 and containing 0.3% of sodium laurylsulfate.

The addition of phospholipids induced an acceleration of the dissolution rate of itraconazole, i.e., >20% of the dissolution ratio at 5 min, >35% at 10 min, >60% at 20 min, >90% at 60 min. Result are shown in Table 11.

TABLE 11

Dissolution rate of ITZ

| | Dissolution rate of ITZ (%) | | | |
|---|---|---|---|---|
| Formulation | 5 min | 10 min | 20 min | 60 min |
| Example 3A (INV) | 7.9 | 11.4 | 15.2 | 46.7 |
| Example 3B (INV) | 8.1 | 11.7 | 16.8 | 47.3 |
| Example 3C (INV) | 6.8 | 12.7 | 34.1 | 98 |
| Example 3D (INV) | 24.7 | 37.2 | 64.6 | 96.4 |
| Example 3E (INV) | 19.8 | 36.7 | 68.3 | 96.9 |

Increasing quantity of incorporated phospholipids in the formulation induced acceleration of API's dissolution rate. Indeed, as an example, Example 3C contained 1% (w/w) of phospholipids (expressed by weight of itraconazole) whereas Example 3D contained 10% (w/w). Formulation 3E containing also 10% (w/w) of phospholipids expressed by weigh of itraconazole exhibited a similar dissolution profile than Example 3D, which also contained 10% (w/w) of phospholipids. Although the total amount of phospholipids in the final dry form was much lower for Example 3E (0.99% for Example 3E) this formulation did not show a different dissolution profile than Example 3D which contained a higher total quantity of phospholipids in the final dry form (3.47%).

This indicates that, when evaluated in those conditions, the itraconazole/phospholipids ratio seemed to be the key factor for the API dissolution rate enhancement. It is therefore possible to make vary, to modulate dissolution velocity within this range by varying this ratio. This could be an advantage in vivo to offer different possibility of drug intrapulmonary pharmacokinetic.

Regarding this it is possible to produce a formulation, possessing high fine particle fraction, with a faster dissolution rate than bulk material. But it is also possible to control/modulate this acceleration by varying the quantity of incorporated surfactant.

Example 4

The purpose of this example was to show the ability of the invention to produce matricial dry powders with high fine particle fractions, improved wettability, different dissolution profile and good flow properties using high potentially healthy safe hydrophobic matrix farming agents.

The formulation was prepared at laboratory scale by spray-drying using a Büchi Mini Spray Dryer B-191a (Büchi laboratory-Techniques, Switzerland). A determined quantity of itraconazole, cholesterol and hydrogenated soy-lecithin with more than 90% of hydrogenated phosphatidylcholine (Phospholipon 90H) (see Table 12) were dissolved in 100 ml of isopropanol heated at 70° C. under magnetic stirring (600 rpm). The solution was spray-dried in the following conditions: spraying air flow, 800 l/h heated at 50° C.; drying air flow, 35 m$^3$/h; solution feed rate, 2.7 g/min; nozzle size, 0.5 mm; Inlet temperature, 70° C.; resulting outlet temperature, 45° C.

TABLE 12

Composition of the spray-dried solutions in Example 4

| Liquid composition | Composition (g/100 ml) |
| --- | --- |
| Example 4 (INV) | Itraconazole 0.525 g |
|  | Cholesterol 1.5 g |
|  | Phospholipon 90H 0.0525 g |

CI value was estimated, as described in Example 1, at 18.9% indicating good powder flowability.

Particle size measurement (Table 13) analysis showed that formulation 4 presented a volume median particle diameter of about 1.1 µm with the Mastersizer2000® and 2.9 µm with the Spraytec®. Some agglomerates seemed to be present in the formulation with higher d(0.9) values. They were probably formed by a certain softening of the phospholipid during the spray drying process due to outlet temperature close of its glass transition.

TABLE 13

Size distribution parameters measured by laser diffraction methods for the formulation of Example 4

| Formulation N = 3 | Mastersizer Sirocco 2000® | | Malvern Spraytec® | |
| --- | --- | --- | --- | --- |
|  | d(0.5) (µm) | d(0.9) (µm) | d(0.5) (µm) | d(0.9) µm |
| Example 4 | 1.13 ± 0.03 | 7.20 ± 1.57 | 2.94 ± 0.07 | 9.35 ± 0.19 |

This presence of agglomerates influenced particles deposition evaluated during aerodynamic assessment of fine particles test realized as described in Example 1. However, 44% of the loaded dose for Example 4 reached the three lower stages of the impactor (table 14).

TABLE 14

Particle deposition in mg (mean ± SD) and FPF obtained during impaction test (MSLI, 100 l/min, 2.4 sec, 3 discharges per test, nominal dose weighted at 2.5 mg, n = 3).

|  | Example 4 |
| --- | --- |
| Device (mg) | 0.73 ± 0.05 |
| Throat (mg) | 0.15 ± 0.03 |
| Stage 1 (mg) | 0.26 ± 0.14 |
| Stage 2 (mg) | 0.17 ± .08 |
| Stage 3 (mg) | 0.31 ± 0.03 |
| Stage 4 (mg) | 0.50 ± 0.05 |
| Stage 5 (mg) | 0.28 ± 0.03 |
| Mean FPD (mg) | 1.1 ± 0.1 |
| Mean FPF (%) | 44 ± 4 |

Dissolution test were performed as described in Example 1 but the dissolution media was constituted of desionized water set at pH 1.2 (HCl 0.063N) containing 1% of sodium lauryl sulfate (FIG. 11). Formulation 4 presented a faster dissolution rate than crystalline micronized bulk itraconazole.

The use of a hydrophobic GRAS matrix former directly modified the release profile of the dispersed API while providing good aerodynamic characteristics and flow properties.

Example 5

The purpose of this example is to show the influence of API's physical state (amorphous Vs crystalline nanoparticles) in the formulation. Two formulations presenting the same quantitative composition were produced and characterized. However the API was in a different physical state in each formulation.

The formulations 5A and 5B were obtained by spray drying a solution or a nanosuspension, respectively, using a Büchi Mini Spray Dryer B-191a (Büchi laboratory-Techniques, Switzerland).

For Example 5A the dry powder was produced by spray drying a feed stock solution of both excipient and API. 0.10 g of itraconazole, 0.9 g of mannitol and 0.01 g of TPGS 1000 were dissolved in 100 ml of an hydro-alcoholic solution (20 water:80 isopropanol) heated at 70° C. under magnetic stirring (600 rpm). This solution was spray-dried in the following conditions: spraying air flow, 800 l/h; drying air flow, 35 m$^3$/h; solution feed rate, 2.7 g/min; nozzle size, 0.5 mm; Inlet temperature, 90° C.; resulting outlet temperature of 53° C.

For Example 5B the dry powder was produced by spray drying a feed stock solution of excipients in which was re-suspended a determined volume of API nanosuspension added prior spray drying. This procedure was composed of two steps. The first one consisted in size reduction of a micronized API suspension to a nanosize range suspension. The second one consisted to re-suspend a determined quantity of the produced nanoparticles in a feed stock solution containing the matricial agent in order to spray-dry it.

The nanosuspension was prepared as following. In 75 ml of a hydro-alcoholic solution (isopropanol 25:water 50) 75 mg of TPGS 1000 were dissolved under magnetic stirring (600 rp). 750 mg of micronized itraconazole were suspended in this solution using a CAT high speed homogenizer X620 (HSH) (CAT M. Zipperer, Staufen, Germany) at 24,000 rpm during 5 min. The suspension was then circulated in a high pressure homogenizer EmulsiFlex C5 (Avestin Inc., Ottawa, Canada) at 24000 PSI until the particles presented a d(0.5) under 300 nm and a d(0.9) under 2.5 μm. Particle size distribution analysis of the homogenized suspension was done by laser diffraction with a wet sampling system (Mastersizer, Hydro 2000, Malvern instruments, UK). For measurements samples were dispersed in deionized water saturated in itraconazole containing 2% of poloxamer 407 to avoid particle dissolution and aggregation. A refractive index of 1.61 and an absorption index of 0.01 were used for measurements. The high pressure homogenization was done using a heat exchanger, placed ahead of the homogenizing valve to maintain sample temperature below 10° C. 270 ml of a hydro-alcoholic solution composed of 200 ml of isopropanol and 70 ml of water, wherein 2.7 g of mannitol was dissolved under magnetic stirring, was prepared. This solution was kept in an ice bath and 30 ml of the produced nanosuspension was added under magnetic stirring (200 rpm). This final suspension was spray-dried. The following conditions were used during spray-drying: spraying air flow, 800 l/h; drying air flow, 35 m³/h; solution feed rate, 2.7 g/min; nozzle size, 0.5 mm; Inlet temperature, 80° C.; resulting outlet temperature, 45° C.

The composition of final dry products is shown in Table 15.

TABLE 15

Quantitative composition of final dry products of Example 5

| Formulation | Quantitative composition of the dry product |
| --- | --- |
| Example 5A (INV) | Itraconazole 9.9%<br>Mannitol 89.1%<br>TPGS 1000 0.9% |
| Example 5B (INV) | Itraconazole 9.9%<br>Mannitol 89.1%<br>TPGS 1000 0.9% |

Particle size distribution measurement of the prepared nanosuspension was done. The suspension presented a d(0.5) and a d(0.9) of 0.257+/−0.005 μm and 1.784+/−0.010 μm, respectively. The two dry sample presented good powder flowability. Carr's index values were 19.9% and 24.7% for Examples 5A and 5B, respectively.

PDRX analysis showed that for formulation 5A no characteristics diffraction's peak of crystalline itraconazole were present while the diffractogram of Example 5B exhibited it clearly. Itraconazole was then present in formulation 5A in an amorphous state while it was in a nano-crystalline state in formulation 5B.

Malvern Sirocco® particle size analysis revealed very close size distributions values for both formulations. Results are shown in Table 16. In contrast with those results, Spraytec measurement revealed that after discharge from an inhaler device formulation 5B exhibited a totally different size distribution profile (see in Tables 16). Indeed, the presence of severe agglomerates was observed graphically and traduced by a severe increase of the d(0.9) value to 64.50±19.9 μm.

TABLE 16

Size distributions parameters measured by laser diffraction with a Malvern Sirocco ® and Spraytec ® for the formulation of Example 5

| Formulation N = 3 | Mastersizer Sirocco 2000 ® | | Malvern Spraytec ® | |
| --- | --- | --- | --- | --- |
| | d(0.5) (μm) | d(0.9) (μm) | d(0.5) (μm) | d(0.9) (μm) |
| Example 5A (INV) | 1.60 ± 0.14 | 3.59 ± 0.25 | 4.33 ± 0.63 | 9.12 ± 0.74 |
| Example 5B (INV) | 1.72 ± 0.07 | 3.61 ± 0.15 | 6.30 ± 1.1 | 64.50 ± 19.9 |

Formulation 5B seemed to present lower deagglomeration efficiency than formulation 5A in simulated breath condition. However, despite this presence of severe agglomerates formulation 5B presented the higher fine particle fraction determined as described in Example 1 (see Table 17).

TABLE 17

Particle deposition in mg (mean ± SD) and fine particle fraction expressed in % of nominal dose (FPF) obtained during impaction test (MSLI, 100 l/min, 2.4 sec, 3 discharges per test, nominal dose weighted at 2.5 mg, n = 3)

| | Example 5A | Example 5B |
| --- | --- | --- |
| Device (mg) | 0.27 ± 0.01 | 0.44 ± 0.02 |
| Throat (mg) | 0.49 ± 0.02 | 0.28 ± 0.01 |
| Stage 1 (mg) | 0.24 ± 0.01 | 0.13 ± 0.03 |
| Stage 2 (mg) | 0.37 ± 0.01 | 0.25 ± 0.04 |
| Stage 3 (mg) | 0.62 ± 0.01 | 0.68 ± 0.03 |
| Stage 4 (mg) | 0.31 ± 0.0 | 0.47 ± 0.02 |
| Stage 5 (mg) | 0.04 ± 0.0 | 0.08 ± 0.0 |
| Mean FPD (mg) | 0.95 +/− 0.1 | 1.19 +/− 0.03 |
| Mean FPF (%) | 38 +/− 4 | 48 +/− 1.2 |

Dissolution tests were conducted using the method described in Example 1. The two formulations presented different dissolution rates. Formulation 5B exhibited a faster dissolution rate than formulation 5A but the two formulations presented faster dissolution rate than bulk itraconazole.

Example 6

The invention can also consist in a blend of crystalline nanoparticles matricial formulation and the amorphous matricial formulations to vary the dissolution profile of the active ingredient in the desire range. The blend can be realized before or during capsule filling. The burst effect that would be provided by the nanoparticles will induce a determined concentration of ITZ that could be enhanced at a desired velocity by dissolution of the amorphous matricial formulation for which the dissolution rate could be optimized. The proportion of matricial formulation nanoparticle formulation in the final blend will determine to which extend the burst effect (rapid initial dissolution of the drug) would be pronounced.

What is claimed is:

1. Spray-dried particles for an inhalation composition, comprising:
   a) between 5 and 50% by weight, based on a total dry particle weight of the composition, of at least one azole compound consisting of iconazole, fluconazole, itraconazole, posaconazole, voriconazole, isoconazole, ketoconazole, oxiconazole, bifoconazole, fentoconazole, tioconazole, terconazole, sulconazole, ravuconazole, econazole, and mixtures thereof in an amorphous state; and up to 20 wt. % of the total dry particle weight of at least one azole compound having a nanocrystaline structure with a mean size of between 0.1 and 1 micrometers, wherein said composition attains about 100% dissolution in less than 20 minutes; and
   b) at least one matricidal compound comprising a polyol comprising sorbitol, mannitol or xylitol; a monosaccharide comprising glucose or arabinose; a disaccharide comprising lactose, maltose, saccharose or dextrose; cholesterol or any mixture thereof.

2. The particles of claim 1, wherein the matricidal compound is mannitol or cholesterol.

3. The particles of claim 1, wherein a weight ratio of the at least one azole compound and at least one matricidal compound is between 0.5/99.5 and 40/60.

4. The particles of claim 1, further comprising a surfactant.

5. The particles of claim 4, comprising between 0.1 and 5% by weight of the surfactant.

6. The particles of claim 4, wherein said surfactant comprises lecithin, phospholipid compounds or hydrogenated phospholipid compounds, or alpha-tocopherol compounds.

7. The particles of claim 6, wherein said phospholipid compounds comprise phosphatic acids, saturated or unsaturated phosphatidyl choline, phosphatidyl ethanol amine, phosphatidyl glycerol, phosphatidyl serine, phosphatidyl inositol, dioleoylphosphatidylcholine, dimyristoyl phosphatidylcholine, dipalmitoyl phosphatidylcholine, distearolyl phosphatidylcholine, dibenolyl phosphatidylcholine, ditricosanoyl phosphatidylcholine, diarachinolyl phosphatidylcholine, dilignocerolyl phosphatidylcholine, dimyristoyl phosphatidyl ethanol amine, dipalmitoyl, phosphatidyl ethanol amine, pipalmitoleoyl phosphatidyl ethanol amine, distearolyl phosphatidyl ethanol amine, dimyristolyl phosphatidyglycerol, or dipalmitoylphosphatidyl glycerol.

8. The particles of claim 1, which provide a Fine Particle Fraction of the azole compound of at least 35% of the total nominal dose of the azole in the particles in accordance with the method "Preparations for Inhalation: Assessment of Fine Particles" using a Multi-Stage Liquid Impinger, Apparatus C, chapter 2.9.18 of the European Pharmacopeia.

9. The particles of claim 5, which contain between about 0.5 and 5% by weight of said surfactant.

10. A method for preparing the spray-dried particles of claim 1, which comprises the steps of:
    a) preparing a liquid composition, comprising:
        i) a liquid carrier, comprising a class 3 solvent according to European Pharmacopeia; selected from the group consisting of acetic acid, heptane, acetone, isobutyl acetate, anisole, isopropyl acetate, 1-butanol, methyl acetate, 2-butanol, 3-methyl-1-butanol, butyl acetate, methyl ethyl ketone, tert-butyl methyl ether, methyl isobutyl ketone, cumene, 2-methyl-1-propanol, dimethyl sulfoxide, and pentane;
        ii) a liquid carrier, selected from the group consisting of ethanol, 1-propanol, ethyl ether, 2-propanol, ethyl formate, propyl acetate, formic acid, mixtures thereof, and any mixtures of the above with water; and
        iii) at least one azole compound in solution in any of said liquid carriers i) or ii) or both; and
        iv) at least one matricidal compound in solution in any of said liquid carriers i) or i) or both; and
    b) spray-drying the liquid composition thereby producing said particles.

11. The method of claim 10, wherein the liquid composition comprises a mixture of class 3 solvents from European Pharmacopeia, or any mixture of two or more of such solvents with or without water.

12. The method of claim 10, wherein said liquid carrier further comprises a surfactant.

13. The method of claim 10, wherein the at least one azole compound is itraconazole.

14. The particles of claim 1, wherein said at least one azole compound is itraconazole.

15. The particles of claim 1, wherein both said amorphous and said nanocrystalline at least one azole compound are itraconazole.

* * * * *